United States Patent
Flannery et al.

(10) Patent No.: US 7,893,029 B2
(45) Date of Patent: Feb. 22, 2011

(54) RECOMBINANT LUBRICIN MOLECULES AND USES THEREOF

(75) Inventors: Carl Ralph Flannery, Acton, MA (US); Christopher John Corcoran, Arlington, MA (US); Bethany Annis Freeman, Arlington, MA (US); Lisa A. Collins-Racie, Acton, MA (US)

(73) Assignee: Wyeth LLC, Madison, NJ (US)

( * ) Notice: Subject to any disclaimer, the term of this patent is extended or adjusted under 35 U.S.C. 154(b) by 0 days.

(21) Appl. No.: 12/622,141

(22) Filed: Nov. 19, 2009

(65) Prior Publication Data

US 2010/0074935 A1    Mar. 25, 2010

Related U.S. Application Data

(62) Division of application No. 10/567,764, filed as application No. PCT/US2004/026508 on Aug. 13, 2004, now Pat. No. 7,642,236.

(60) Provisional application No. 60/495,741, filed on Aug. 14, 2003.

(51) Int. Cl.
*A61K 38/39* (2006.01)
*C07K 14/47* (2006.01)
*C12P 21/02* (2006.01)

(52) U.S. Cl. .................... 514/12; 530/350; 435/69.1
(58) Field of Classification Search ............. 514/12; 530/350; 435/69.1
See application file for complete search history.

(56) References Cited

U.S. PATENT DOCUMENTS

| | | | |
|---|---|---|---|
| 2,487,377 | A | 11/1949 | Roehner et al. |
| 2,734,862 | A | 2/1956 | Morway et al. |
| 2,878,184 | A | 3/1959 | March |
| 4,108,849 | A | 8/1978 | Thomas |
| 4,438,100 | A | 3/1984 | Balslev et al. |
| 5,260,417 | A | 11/1993 | Grant et al. |
| 5,326,558 | A | 7/1994 | Turner et al. |
| 5,403,592 | A | 4/1995 | Hills |
| 5,510,121 | A | 4/1996 | Rhee et al. |
| 5,510,122 | A | 4/1996 | Sreebny et al. |
| 5,515,590 | A | 5/1996 | Pienkowski |
| 5,605,938 | A | 2/1997 | Roufa et al. |
| 5,612,028 | A | 3/1997 | Sackier et al. |
| 5,639,796 | A | 6/1997 | Lee |
| 5,702,456 | A | 12/1997 | Pienkowski |
| 5,709,020 | A | 1/1998 | Pienkowski et al. |
| 6,433,142 | B1 | 8/2002 | Turner et al. |
| 6,743,774 | B1 | 6/2004 | Jay |
| 6,960,562 | B2 | 11/2005 | Jay |
| 7,001,881 | B1 | 2/2006 | Jay |
| 2004/0229804 | A1 | 11/2004 | Jay |

FOREIGN PATENT DOCUMENTS

| | | |
|---|---|---|
| AU | 781564 | 1/2001 |
| CA | 2367750 | 11/2000 |
| EP | 1440981 | 7/2004 |
| WO | WO 92/13075 | 8/1992 |
| WO | WO 95/23861 | 9/1995 |
| WO | WO 00/64930 | 11/2000 |
| WO | WO 01/07068 | 2/2001 |
| WO | WO 02/062847 | 8/2002 |

OTHER PUBLICATIONS

Alignment of instant SEQ ID No. 11 with the MSF polypeptide of Turner et al., WO 92/13075 A1, GenBank record No. AAR26049, Result 6 in Geneseq database search of Feb. 19, 2010.*
Aydelotte et al., "Heterogeneity of Articular Chondrocytes," Articular Cartilage and Osteoarthritis, Raven Press Ltd., New York, pp. 237-249 (1992).
Caron, J.P., "Understanding the Pathogenesis of Equine Osteoarthritis," *Br. Vet. J. Sci., USA*, 149:369-371 (1992).
Chambers et al., "Matrix Metalloproteinases and Aggrecanases Cleave Aggrecan in Different Zones of Normal Cartilage but Colocalize in the Development of Osteoarthritic Lesions in STR/ort Mice," *Arthritis & Rheumatism*, 44(6):1455-1465 (2001).
Davis et al., "A proposed model of boundary lubrication by synovial fluid: structuring of boundary water," *Journal of Biomechanical Engineering*, 101:185-192 (Aug. 1979).
Espallargues and Pons, "Efficacy and Safety of Viscosupplementation with Hylan G-F 20 for the Treatment of Knee Osteoarthritis: A Systematic Review," *International Journal of Technology Assessment in Health Care*, 19(1):41-56 (2003).
European Search Report dated Jul. 6, 2009 for related European Appl. No. 04781229.2.
Flannery et al., "Articular Cartilage Superficial Zone Protein (SZP) is Homologous to Megakaryocyte Stimulating Factor Precursor and is a Multifunctional Proteoglycan with Potential Growth-Promoting, Cytoprotective, and Lubricating Properties in Cartilage Metabolism," *Biochemical and Biophysical Research Communications*, 254:535-541 (1999).
Garg et al., "The Structure of the O-Glycosylically-linked Oligosacharide Chains of LPG-I, A Glycoprotein Present in Articular Lubricating Fraction of Bovine Synovial Fluid," *Carbohydrate Research*, 78:79-88 (1979).
Glasson et al., "Characterization of and Osteoarthritis Susceptibility in ADAMTS-4-Knockout Mice," *Arthritis & Rheumatism*, 50(8):2547-2558 (2004).
Goldberg et al., "Prevention of Postoperative Adhesions by Precoating Tissues with Dilute Sodium Hyaluronate Solutions," In: *Gynecologic Surgery and Adhesion Prevention*, (Willey-Liss), pp. 191-204 (1993).
Hills et al., "Deficiency of lubricating surfactant lining the articular surfaces of replaced hips and knees," *British Journal of Rheumatology*, 37:143-147 (1998).

(Continued)

*Primary Examiner*—Karen Cochrane Carlson
*Assistant Examiner*—Rosanne Kosson

(57) ABSTRACT

Recombinant lubricin molecules and uses thereof. Novel recombinant lubricin molecules and their uses as lubricants, anti-adhesive agents and/or intra-articular supplements for, e.g., synovial joints, meniscus, tendon, peritoneum, pericardium and pleura, are provided.

20 Claims, No Drawings

OTHER PUBLICATIONS

Hills et al., "Ezymatic identification of the load-bearing boundary lubricant in the joint," British *Journal of Rheumatology*, 37:137-142 (1998).

Hills, Brian A., "Identity of the Joint Lubricant," *The Journal of Rheumatology*, 29:200-201 (2002).

Ikegawa et al., "Isolation, characterization and mapping of the mouse and human PRG4 (proteoglycan 4) genes," *Cytogenet. Cell Genet.*, 90:291-297 (2000).

Jay et al, "Homology of lubricin and superficial zone protein (SZP): products of megakaryocyte stimulating factor (MSF) gene expression by human synovial fibroblasts and articular chondrocytes localized to chromosome 1q25," *J. Orthop. Res.*, 19:677-687, (2001).

Jay et al., "Boundary lubrication by lubricin is mediated by O-linked β(1-3)Gal-GalNAc oligosaccharides," *Glycoconjugate Journal*, 18:807-815 (2001).

Jay et al., "Comparison of the boundary-lubricating ability of bovine synovial fluid, lubricin, and Healon," *Biomed. Mater. Res.*, 40:414-418 (1998).

Jay et al., "Lubricin is a product of megakaryocyte stimulating factor (MSF) gene expression by human synovial fibroblasts," *American College of Rheumatology*, vol. 42, No. 9 (Supplement) (Sep. 1999).

Jay et al., "Silver Staining of Extensively Glycosylated Proteins on Sodium Dodecyl Sulfate-Polyacrylamide Gels: Enhancement by Carbohydrate-Binding Dyes," *Analytical Biochemistry*, 185:324-330 (1990).

Jay, "Characterization of a Bovine Synovial Fluid Lubricating Factor. I. Chemical, Surface Activity and Lubricating Properties," *Connective Tissue Research*, 28:71-88 (1992).

Jay et al., "Characterization of a Bovine Synovial Fluid Lubricating Factor. II. Comparison with Purified Ocular and Salivary Mucin," *Connective Tissue Research*, 28:89-98 (1992).

Jay et al., "Characterization of a Bovine Synovial Fluid Lubricating Factor. III. The Interaction with Hyaluronic Acid," *Connective Tissue Research*, 28:245-255 (1992).

Jay, Gregory D., "Joint lubrication: A physicochemical study of a purified lubricating factor from bovine synovial fluid," State University of New York at Stony Brook (1990).

Jay, Gregory, "Lubricin and surfacing of articular joints," *Curr. Opin. Orthop.*, 15:355-359 (2004).

Krstenansky and Mao, "Antithrombin properties of C-terminus of hirudin using synthetic unsulfated $N^\alpha$-acetyl-hirudin$_{45-65}$," *FEBS Letter*, 211(1):10-16 (1987).

Lorenzo et al., "A Novel Cartilage Protein (CILP) Present in the Mid-zone of Human Articular Cartilage Increases with Age," *J. of Biol. Chem.* 273(36):23463-23468 (1998).

Lorenzo et al., "Cloning and Deduced Amino Acid Sequence of a Novel Cartilage Protein (CLIP) Identifies a Profrom Including a Nucleotide Pyrophosphohydrolase," *J. Biol. Chem.*, 273(36):23469-23475 (1998).

Marcelino et al., "CACP, encoding a secreted proteoglycan, is mutated in camptodactyly-arthropathy-coxa vara-pericarditis syndrome," *Nature Genetics*, 23:319-322 (1999).

Marcelino et al., "Mutations in a secreted proteoglycan cause a human disease characterized by synovial and pericardial cell hyperplasia," Abstracts Presented at the 39th American Society for Cell Biology Annual Meeting, Washington, DC (Dec. 11-15, 1999).

Marcelino et al., "The gene for the camptodactyly-arthropathy-coxa vara-pericarditis syndrome (CACP) encodes a secreted proteoglycan that is essential to normal joint function," *The American Journal of Human Genetics*, vol. 65, No. 4 (Oct. 1999), Abstract only.

Merberg et al., "A Comparison of Vitronectin and Megakaryocyte Stimulating Factor," *Biology of Vitronectin and their Receptors*, Preissner and et al., Editors, Elsevier Science, Amsterdam, pp. 45-53 (1993).

Merrifield, R. B., "Solid Phase Peptide Synthesis. I. The Synthesis of a Tetrapeptide," *J. Amer. Chem. Soc.*, 85:2149-2154 (1963).

Morawietz et al., "Differential gene expression in the periprosthetic membrane: lubricin as a new possible pathogenetic factor in prosthesis loosening," *Virchows Arch*, 443:57-66 (2003).

Rees et al., "Immunolocalisation and expression of proteoglycan 4 (cartilage superficial zone proteoglycan) in tendon," *Matrix Biology*, 21:593-602 (2002).

Results 1, 3, 5, 7, 9, 11, 13 and 15, alignments of instant SEQ ID No. 7 with polypeptides of Turner et al., US 6,433,142, from a search in the database of sequences from issued U.S. Patents, searched on Dec. 28, 2007, 11 pages.

Results 1, 2, 10, 12 and 14, alignments of instant SEQ ID No. 7 with polypeptides of Turner et al., US 6,433,142, from a search in the database of sequences from issued U.S. Patents, searched on Dec. 11, 2007, 24 pages.

Schaefer et al., "Lubricin reduces cartilage-cartilage integration," *Biorheology*, 41:503-508 (2004).

Schneerson et al., "Preparation, characterization, and immunogenicity of *Haemophilus influenzae* Type b Polysaccharide-Protein Conjugates," *The Journal of Experimental Medicine*, 152:361-376 (1980).

Schumacher et al., "A Novel Proteoglycan Synthesized and Secreted by Chondrocytes of the Superficial Zone of Articular Cartilage," *Archives of Biochemistry and Biophysics*, 311:144-152 (1994).

Schumacher et al., "Immunodetection and partial cDNA sequence of the proteoglycan, superficial zone protein, synthesized by cells lining synovial joints," *Journal of Orthopaedic Research*, 17:110-120 (1999).

Schumacher, Jr., H. Ralph, "Aspiration and Injection Therapies for Joints," *Arthritis & Rheumatism*, 49(3):413-420 (2003).

Schwarz et al., "Surface-active phospholipid as the lubricating component of lubricin," *British Journal of Rheumatology*, 37:21-26 (1998).

Swann et al., "Evidence that lubricating glycoprotein-I (LGP-I) is the molecule responsible for the unique lubricating properties of bovine synovial fluid in a cartilage on glass test system," Biology of the Articular Cartilage in Health and Disease, Proceedings of the Second Munich Symposium on Biology of Connective Tissue, Munich, ed. H. Gastpar (Jul. 23-24, 1979).

Swann et al., "The Lubricating Activity of Synovial Fluid Glycoproteins," *Arthritis and Rheumatism*, 24(1):22-30 (1981).

Swann et al., "The molecular structure and lubricating activity of lubricin isolated from bovine and human synovial fluids," *Biochem. J.*, 225:195-201 (1985).

Swann et al., "The Molecular Structure of Lubricating Glycoprotein-I, the Boundary Lubricant for Articular Cartilage," *The Journal of Biological Chemistry*, 256(11):5921-5925 (1981).

Tatusova and Madden, "BLAST 2 Sequences, a new tool for comparing protein and neucleotide sequences," *FEMS Microbiology Letters*, 174:247-250 (1999).

Turner et al., "Purification, Biochemical Characterization and Cloning of a Novel Megakaryocyte Stimulating Factor that has Megakaryocyte Colony Stimulating Activity," *Blood*, 78(Suppl. 1): 279 (1991).

Wobig et al., "Viscosupplementation with Hylan G-F 20: A 26-Week Controlled Trial of Efficacy and Safety in the Osteoarthritic Knee," *Clinical Therapeutics*, 20(3):410-423 (1998).

Wobig et al., "The Role of Elastoviscosity in the Efficacy of Viscosupplementation for Osteoarthritis of the Knee: A Comparison of Hylan G-F 20 and a Lower-Molecular-Weight Hyaluronan," *Clinical Therapeutics*, 21(9):1549-1562 (1999).

\* cited by examiner

SEQUENCE LISTING

<160> NUMBER OF SEQ ID NOS: 29

<210> SEQ ID NO 1
<211> LENGTH: 155
<212> TYPE: DNA
<213> ORGANISM: Artificial Sequence
<220> FEATURE:
<223> OTHER INFORMATION: Nucleotide sequence of synthetic cDNA
      cassette-1.

<400> SEQUENCE: 1
cgcgcccaca actccaaaag agcccgcacc taccacgaca aagtcagctc ctactacgcc      60
caaagagcca gcgccgacga ctactaaaga accggcaccc accacgccta aggagccagc     120
tcctactaca acgaaaccgg caccaaccac tccgg                                155

<210> SEQ ID NO 2
<211> LENGTH: 51
<212> TYPE: PRT
<213> ORGANISM: Artificial Sequence
<220> FEATURE:
<223> OTHER INFORMATION: Synthetically generated peptide

<400> SEQUENCE: 2

Ala Pro Thr Thr Pro Lys Glu Pro Ala Pro Thr Thr Thr Lys Ser Ala
1               5                   10                  15

Pro Thr Thr Pro Lys Glu Pro Ala Pro Thr Thr Thr Lys Glu Pro Ala
            20                  25                  30

Pro Thr Thr Pro Lys Glu Pro Ala Pro Thr Thr Thr Lys Pro Ala Pro
        35                  40                  45

Thr Thr Pro
    50

<210> SEQ ID NO 3
<211> LENGTH: 125
<212> TYPE: DNA
<213> ORGANISM: Artificial Sequence
<220> FEATURE:
<223> OTHER INFORMATION: Nucleotide sequence of synthetic cDNA
      cassette-2.

<400> SEQUENCE: 3
taaagaacca gcccctacta cgacaaagga gcctgcaccc acaaccacga agagcgcacc      60
cacaacacca aaggagccgg cccctacgac tcctaaggaa cccaaaccgg caccaaccac     120
tccgg                                                                125

<210> SEQ ID NO 4
<211> LENGTH: 41
<212> TYPE: PRT
<213> ORGANISM: Artificial Sequence
<220> FEATURE:

-continued

<223> OTHER INFORMATION: Synthetically generated peptide

<400> SEQUENCE: 4

```
Lys Glu Pro Ala Pro Thr Thr Lys Glu Pro Ala Pro Thr Thr Thr
1               5                  10                  15

Lys Ser Ala Pro Thr Thr Pro Lys Glu Pro Ala Pro Thr Thr Pro Lys
            20                  25                  30

Glu Pro Lys Pro Ala Pro Thr Thr Pro
            35                  40
```

<210> SEQ ID NO 5
<211> LENGTH: 8049
<212> TYPE: DNA
<213> ORGANISM: Artificial Sequence
<220> FEATURE:
<223> OTHER INFORMATION: pTmed2 vector containing recombinant PRG4-Lub:1 cDNA construct.

<400> SEQUENCE: 5

| | | | |
|---|---|---|---|
| catatgcggt gtgaaatacc gcacagatgc gtaaggagaa ataccgcat caggcgtact | | | 60 |
| gagtcattag ggactttcca atgggttttg cccagtacat aaggtcaata ggggtgaatc | | | 120 |
| aacaggaaag tcccattgga gccaagtaca ctgagtcaat agggactttc cattgggttt | | | 180 |
| tgcccagtac aaaaggtcaa taggggtga gtcaatgggt ttttcccatt attggcacgt | | | 240 |
| acataaggtc aataggggtg agtcattggg tttttccagc caatttaatt aaaacgccat | | | 300 |
| gtactttccc accattgacg tcaatgggct attgaaacta atgcaacgtg acctttaaac | | | 360 |
| ggtactttcc catagctgat taatgggaaa gtaccgttct cgagccaata cacgtcaatg | | | 420 |
| ggaagtgaaa gggcagccaa aacgtaacac cgccccggtt ttccctgga aattccatat | | | 480 |
| tggcacgcat tctattggct gagctgcgtt ctacgtgggt ataagaggcg cgaccagcgt | | | 540 |
| cggtaccgtc gcagtcttcg gtctgaccac cgtagaacgc agagctcctc gctgcagccc | | | 600 |
| aagctctgtt gggctcgcgg ttgaggacaa actcttcgcg gtctttccag tactcttgga | | | 660 |
| tcggaaaccc gtcggcctcc gaacggtact ccgccaccga gggacctgag cgagtccgca | | | 720 |
| tcgaccggat cggaaaacct ctcgactgtt ggggtgagta ctccctctca aaagcgggca | | | 780 |
| tgacttctgc gctaagattg tcagtttcca aaaacgagga ggatttgata ttcacctggc | | | 840 |
| ccgcggtgat gcctttgagg gtggccgcgt ccatctggtc agaaaagaca atcttttgt | | | 900 |
| tgtcaagctt gaggtgtggc aggcttgaga tctggccata cacttgagtg acaatgacat | | | 960 |
| ccactttgcc tttctctcca caggtgtcca ctcccaggtc caactgcaga cttcgaattc | | | 1020 |
| tactgagtcg acccaccatg gcatggaaaa cacttcccat ttacctgttg ttgctgctgt | | | 1080 |
| ctgttttcgt gattcagcaa gtttcatctc aagatttatc aagctgtgca gggagatgtg | | | 1140 |
| gggaagggta ttctagagat gccacctgca actgtgatta aactgtcaa cactacatgg | | | 1200 |
| agtgctgccc tgatttcaag agagtctgca ctgcggagct ttcctgtaaa ggccgctgct | | | 1260 |
| ttgagtcctt cgagagaggg agggagtgtg actgcgacgc ccaatgtaag aagtatgaca | | | 1320 |
| agtgctgtcc cgattatgag agtttctgtg cagaagtgca taatcccaca tcaccaccat | | | 1380 |
| cttcaaagaa agcacctcca ccttcaggag catctcaaac catcaaatca acaaccaaac | | | 1440 |
| gttcacccca accaccaaac aagaagaaga ctaagaaagt tatagaatca gaggaaataa | | | 1500 |
| cagaagaaca ttctgttttct gaaaatcaag agtcctcctc cagtagcagt tcaagtagtt | | | 1560 |
| cgtcgtcgac aatttggaaa atcaagtctt ccaaaaattc agctgctaat agagaattac | | | 1620 |
| agaagaaact caaagtaaaa gataacaaga gaacagaac taaaaagaaa cctacccca | | | 1680 |

```
aaccaccagt tgtagatgaa gctggaagtg gattggacaa tggtgacttc aaggtcacaa    1740
ctcctgacac gtctaccacc caacacaata aagtcagcac atctcccaag atcacaacag    1800
caaaaccaat aaatcccaga cccagtcttc cacctaattc tgatacatct aaagagacgt    1860
ctttgacagt gaataaagag acaacagttg aaactaaaga aactactaca acaaataaac    1920
agacttcaac tgatggaaaa gagaagacta cttccgctaa agagacacaa agtatagaga    1980
aaacatctgc taaagattta gcacccacat ctaaagtgct ggctaaacct acacccaaag    2040
ctgaaactac aaccaaaggc cctgctctca ccactcccaa ggagcccacg cccaccactc    2100
ccaaggagcc tgcatctacc acacccaaag agcccacacc taccaccatc aagagcgcgc    2160
ccacaactcc aaaagagccc gcacctacca cgacaaagtc agctcctact acgcccaaag    2220
agccagcgcc gacgactact aaagaaccgg cacccaccac gcctaaggag ccagctccta    2280
ctacaacgaa accggcacca accactccgg aaacacctcc tccaaccact tcagaggtct    2340
ctactccaac taccaccaag gagcctacca ctatccacaa aagccctgat gaatcaactc    2400
ctgagctttc tgcagaaccc acaccaaaag ctcttgaaaa cagtcccaag gaacctggtg    2460
tacctacaac taagacgccg gcggcgacta aacctgaaat gactacaaca gctaaagaca    2520
agacaacaga aagagactta cgtactacac ctgaaactac aactgctgca cctaagatga    2580
caaaagagac agcaactaca acagaaaaaa ctaccgaatc caaaataaca gctacaacca    2640
cacaagtaac atctaccaca actcaagata ccacaccatt caaaattact actcttaaaa    2700
caactactct tgcacccaaa gtaactacaa caaaaaagac aattactacc actgagatta    2760
tgaacaaacc tgaagaaaca gctaaaccaa aagacagagc tactaattct aaagcgacaa    2820
ctcctaaacc tcaaaagcca accaaagcac ccaaaaaacc cacttctacc aaaaagccaa    2880
aaacaatgcc tagagtgaga aaaccaaaga cgacaccaac tccccgcaag atgacatcaa    2940
caatgccaga attgaaccct acctcaagaa tagcagaagc catgctccaa accaccacca    3000
gacctaacca aactccaaac tccaaactag ttgaagtaaa tccaaagagt gaagatgcag    3060
gtggtgctga aggagaaaca cctcatatgc ttctcaggcc ccatgtgttc atgcctgaag    3120
ttactcccga catggattac ttaccgagag tacccaatca aggcattatc atcaatccca    3180
tgctttccga tgagaccaat atatgcaatg gtaagccagt agatggactg actactttgc    3240
gcaatgggac attagttgca ttccgaggtc attatttctg gatgctaagt ccattcagtc    3300
caccatctcc agctcgcaga attactgaag tttggggtat tccttccccc attgatactg    3360
tttttactag gtgcaactgt gaaggaaaaa ctttcttctt taaggattct cagtactggc    3420
gttttaccaa tgatataaaa gatgcagggt accccaaacc aattttcaaa ggatttggag    3480
gactaactgg acaaatagtg gcagcgcttt caacagctaa atataagaac tggcctgaat    3540
ctgtgtattt tttcaagaga ggtggcagca ttcagcagta tatttataaa caggaacctg    3600
tacagaagtg ccctggaaga aggcctgctc taaattatcc agtgtatgga gaaatgacac    3660
aggttaggag acgtcgcttt gaacgtgcta taggaccttc tcaaacacac accatcagaa    3720
ttcaatattc acctgccaga ctggcttatc aagacaaagg tgtccttcat aatgaagtta    3780
aagtgagtat actgtggaga ggacttccaa atgtggttac ctcagctata tcactgccca    3840
acatcagaaa acctgacggc tatgattact atgcctttt taaagatcaa tactataaca    3900
ttgatgtgcc tagtagaaca gcaagagcaa ttactactcg ttctgggcag accttatcca    3960
aagtctggta caactgtcct taagcggccg ccgcaaattc taacgttact ggccgaagcc    4020
```

```
gcttggaata aggccggtgt gcgtttgtct atatgttatt ttccaccata ttgccgtctt    4080
ttggcaatgt gagggcccgg aaacctggcc ctgtcttctt gacgagcatt cctagggggtc   4140 tttcccctct cgccaaagga atgcaaggtc tgttgaatgt cgtgaaggaa gcagttcctc    4200
tggaagcttc ttgaagacaa acaacgtctg tagcgaccct ttgcaggcag cggaaccccc    4260
cacctggcga caggtgcctc tgcggccaaa agccacgtgt ataagataca cctgcaaagg    4320
cggcacaacc ccagtgccac gttgtgagtt ggatagttgg ggaaagagtc aaatggctct    4380
cctcaagcgt attcaacaag gggctgaagg atgcccagaa ggtaccccat tgtatgggat    4440
ctgatctggg gcctcggtgc acatgcttta catgtgttta gtcgaggtta aaaaacgtct    4500 aggcccccg  aaccacgggg acgtggtttt cctttgaaaa acacgattgc tcgagccatc    4560
atggttcgac cattgaactg catcgtcgcc gtgtcccaaa atatggggat tggcaagaac    4620
ggagacctac cctggcctcc gctcaggaac gagttcaagt acttccaaag aatgaccaca    4680
acctcttcag tggaaggtaa acagaatctg gtgattatgg gtaggaaaac ctggttctcc    4740
attcctgaga agaatcgacc tttaaaggac agaattaata tagttctcag tagagaactc    4800
aaagaaccac cacgaggagc tcattttctt gccaaaagtt tggatgatgc cttaagactt    4860
attgaacaac cggaattggc aagtaaagta gacatggttt ggatagtcgg aggcagttct    4920
gtttaccagg aagccatgaa tcaaccaggc cacctcagac tctttgtgac aaggatcatg    4980
caggaatttg aaagtgacac gttttttccca gaaattgatt tggggaaata taaacttctc    5040
ccagaatacc caggcgtcct ctctgaggtc caggaggaaa aaggcatcaa gtataagttt    5100
gaagtctacg agaagaaaga ctaacaggaa gatgctttca agttctctgc tcccctccta    5160
aagctatgca tttttttataa gaccatggga cttttgctgg ctttagatca taatcagcca    5220
taccacattt gtagaggttt tacttgcttt aaaaaacctc ccacacctcc ccctgaacct    5280
gaaacataaa atgaatgcaa ttgttgttgt taacttgttt attgcagctt ataatggtta    5340
caaataaagc aatagcatca caaatttcac aaataaagca ttttttttcac tgcattctag    5400 ttgtggtttg tccaaaactca tcaatgtatc ttatcatgtc tggatccccg gccaacggtc    5460
tggtgacccg gctgcgagag ctcggtgtac ctgagacgcg agtaagccct tgagtcaaag    5520
acgtagtcgt tgcaagtccg caccaggtac tgatcatcga tgctagaccg tgcaaaagga    5580
gagcctgtaa gcgggcactc ttccgtggtc tggtggataa attcgcaagg gtatcatggc    5640
ggacgaccgg ggttcgaacc ccggatccgg ccgtccgccg tgatccatcc ggttaccgcc    5700
cgcgtgtcga acccaggtgt gcgacgtcag acaacggggg agcgctcctt ttggcttcct    5760
tccaggcgcg gcggctgctg cgctagcttt tttggcgagc tcgaattaat tctgcattaa    5820
tgaatcggcc aacgcgcggg gagaggcggt ttgcgtattg ggcgctcttc cgcttcctcg    5880
ctcactgact cgctgcgctc ggtcgttcgg ctgcggcgag cggtatcagc tcactcaaag    5940
gcggtaatac ggttatccac agaatcaggg gataacgcag gaaagaacat gtgagcaaaa    6000
ggccagcaaa aggccaggaa ccgtaaaaag gccgcgttgc tggcgttttt ccataggctc    6060 cgccccctg  acgagcatca aaaaatcga cgctcaagtc agaggtggcg aaacccgaca    6120
ggactataaa gataccaggc gtttccccct ggaagctccc tcgtgcgctc tcctgttccg    6180
accctgccgc ttaccggata cctgtccgcc tttctccctt cgggaagcgt ggcgctttct    6240
caatgctcac gctgtaggta tctcagttcg gtgtaggtcg ttcgctccaa gctgggctgt    6300
gtgcacgaac cccccgttca gcccgaccgc tgcgccttat ccggtaacta tcgtcttgag    6360
tccaacccgg taagacacga cttatcgcca ctggcagcag ccactggtaa caggattagc    6420
```

-continued

| | |
|---|---|
| agagcgaggt atgtaggcgg tgctacagag ttcttgaagt ggtggcctaa ctacggctac | 6480 |
| actagaagga cagtatttgg tatctgcgct ctgctgaagc cagttacctt cggaaaaaga | 6540 |
| gttggtagct cttgatccgg caaacaaacc accgctggta gcggtggttt ttttgtttgc | 6600 |
| aagcagcaga ttacgcgcag aaaaaaagga tctcaagaag atcctttgat cttttctacg | 6660 |
| gggtctgacg ctcagtggaa cgaaaactca cgttaaggga ttttggtcat gagattatca | 6720 |
| aaaaggatct tcacctagat ccttttaaat taaaaatgaa gttttaaatc aatctaaagt | 6780 |
| atatatgagt aaacttggtc tgacagttac caatgcttaa tcagtgaggc acctatctca | 6840 |
| gcgatctgtc tatttcgttc atccatagtt gcctgactcc ccgtcgtgta gataactacg | 6900 |
| atacgggagg gcttaccatc tggccccagt gctgcaatga taccgcgaga cccacgctca | 6960 |
| ccggctccag atttatcagc aataaaccag ccagccggaa gggccgagcg cagaagtggt | 7020 |
| cctgcaactt tatccgcctc catccagtct attaattgtt gccgggaagc tagagtaagt | 7080 |
| agttcgccag ttaatagttt gcgcaacgtt gttgccattg ctacaggcat cgtggtgtca | 7140 |
| cgctcgtcgt ttggtatggc ttcattcagc tccggttccc aacgatcaag gcgagttaca | 7200 |
| tgatccccca tgttgtgcaa aaaagcggtt agctccttcg gtcctccgat cgttgtcaga | 7260 |
| agtaagttgg ccgcagtgtt atcactcatg gttatggcag cactgcataa ttctcttact | 7320 |
| gtcatgccat ccgtaagatg cttttctgtg actggtgagt actcaaccaa gtcattctga | 7380 |
| gaatagtgta tgcggcgacc gagttgctct tgcccggcgt caatacggga taataccgcg | 7440 |
| ccacatagca gaactttaaa agtgctcatc attggaaaac gttcttcggg gcgaaaactc | 7500 |
| tcaaggatct taccgctgtt gagatccagt tcgatgtaac ccactcgtgc acccaactga | 7560 |
| tcttcagcat cttttacttt caccagcgtt tctgggtgag caaaaacagg aaggcaaaat | 7620 |
| gccgcaaaaa agggaataag ggcgacacgg aaatgttgaa tactcatact cttcctttt | 7680 |
| caatattatt gaagcattta tcagggttat tgtctcatga gcggatacat atttgaatgt | 7740 |
| atttagaaaa ataaacaaat aggggttccg cgcacatttc cccgaaaagt gccacctgac | 7800 |
| gtctaagaaa ccattattat catgacatta acctataaaa ataggcgtat cacgaggccc | 7860 |
| tttcgtctcg cgcgtttcgg tgatgacggt gaaaacctct gacacatgca gctcccggag | 7920 |
| acggtcacag cttgtctgta gcggatgcc gggagcagac aagcccgtca gggcgcgtca | 7980 |
| gcgggtgttg gcgggtgtcg gggctggctt aactatgcgg catcagagca gattgtactg | 8040 |
| agagtgcac | 8049 |

<210> SEQ ID NO 6
<211> LENGTH: 2946
<212> TYPE: DNA
<213> ORGANISM: Artificial Sequence
<220> FEATURE:
<223> OTHER INFORMATION: Recombinant PRG4-Lub:1 cDNA construct.

<400> SEQUENCE: 6

| | |
|---|---|
| atggcatgga aaacacttcc catttacctg ttgttgctgc tgtctgtttt cgtgattcag | 60 |
| caagtttcat ctcaagattt atcaagctgt gcagggagat gtgggaagg gtattctaga | 120 |
| gatgccacct gcaactgtga ttataactgt caacactaca tggagtgctg ccctgatttc | 180 |
| aagagagtct gcactgcgga gctttcctgt aaaggccgct gctttgagtc cttcgagaga | 240 |
| gggagggagt gtgactgcga cgcccaatgt aagaagtatg acaagtgctg tcccgattat | 300 |
| gagagtttct gtgcagaagt gcataatccc acatcaccac catcttcaaa gaaagcacct | 360 |

```
ccaccttcag gagcatctca aaccatcaaa tcaacaacca aacgttcacc caaaccacca      420
aacaagaaga agactaagaa agttatagaa tcagaggaaa taacagaaga acattctgtt      480
tctgaaaatc aagagtcctc ctccagtagc agttcaagta gttcgtcgtc gacaatttgg      540
aaaatcaagt cttccaaaaa ttcagctgct aatagagaat tacagaagaa actcaaagta      600
aaagataaca agaagaacag aactaaaaag aaacctaccc ccaaaccacc agttgtagat      660
gaagctggaa gtggattgga caatggtgac ttcaaggtca caactcctga cacgtctacc      720
acccaacaca ataaagtcag cacatctccc aagatcacaa cagcaaaacc aataaatccc      780
agacccagtc ttccacctaa ttctgataca tctaaagaga cgtctttgac agtgaataaa      840
gagacaacag ttgaaactaa agaaactact acaacaaata aacagacttc aactgatgga      900
aaagagaaga ctacttccgc taaagagaca caaagtatag agaaaacatc tgctaaagat      960
ttagcaccca catctaaagt gctggctaaa cctacaccca agctgaaaac tacaaccaaa     1020
ggccctgctc tcaccactcc caaggagccc acgcccacca ctcccaagga gcctgcatct     1080
accacaccca aagagcccac acctaccacc atcaagagcg cgcccacaac tccaaaagag     1140
cccgcaccta ccacgacaaa gtcagctcct actacgccaa aagagccagc gccgacgact     1200
actaaagaac cggcacccac cacgcctaag gagccagctc ctactacaac gaaaccggca     1260
ccaaccactc cggaaacacc tcctccaacc acttcagagg tctctactcc aactaccacc     1320
aaggagccta ccactatcca caaaagccct gatgaatcaa ctcctgagct ttctgcagaa     1380
cccacaccaa aagctcttga aaacagtccc aaggaacctg gtgtacctac aactaagacg     1440
ccggcggcga ctaaacctga aatgactaca acagctaaag acaagacaac agaaagagac     1500
ttacgtacta cacctgaaac tacaactgct gcacctaaga tgacaaaaga gacagcaact     1560
acaacagaaa aaactaccga atccaaaata acagctacaa ccacacaagt aacatctacc     1620
acaactcaag ataccacacc attcaaaatt actactctta aaacaactac tcttgcaccc     1680
aaagtaacta caacaaaaaa gacaattact accactgaga ttatgaacaa acctgaagaa     1740
acagctaaac caaagacag agctactaat tctaaagcga caactcctaa acctcaaaag     1800
ccaaccaaag cacccaaaaa acccacttct accaaaaagc caaaaacaat gcctagagtg     1860
agaaaaccaa agacgacacc aactccccgc aagatgacat caacaatgcc agaattgaac     1920
cctacctcaa gaatagcaga agccatgctc caaaccacca ccagacctaa ccaaactcca     1980
aactccaaac tagttgaagt aaatccaaag agtgaagatg caggtggtgc tgaaggagaa     2040
acacctcata tgcttctcag gccccatgtg ttcatgcctg aagttactcc cgacatggat     2100
tacttaccga gagtacccaa tcaaggcatt atcatcaatc ccatgctttc cgatgagacc     2160
aatatatgca atggtaagcc agtagatgga ctgactactt tgcgcaatgg acattagtt      2220 gcattccgag gtcattattt ctggatgcta agtccattca gtccaccatc tccagctcgc     2280
agaattactg aagtttgggg tattccttcc cccattgata ctgtttttac taggtgcaac     2340
tgtgaaggaa aaactttctt ctttaaggat tctcagtact ggcgttttac caatgatata     2400
aaagatgcag ggtaccccaa accaattttc aaaggatttg gaggactaac tggacaaata     2460
gtggcagcgc tttcaacagc taaatataag aactggcctg aatctgtgta ttttttcaag     2520
agaggtggca gcattcagca gtatatttat aaacaggaac tgtacagaa gtgccctgga      2580 agaaggcctg ctctaaatta ccagtgtat ggagaaatga cacaggttag gagacgtcgc      2640
tttgaacgtg ctataggacc ttctcaaaca cacaccatca gaattcaata ttcacctgcc     2700
agactggctt atcaagacaa aggtgtcctt cataatgaag ttaaagtgag tatactgtgg     2760
```

-continued

```
agaggacttc caaatgtggt tacctcagct atatcactgc ccaacatcag aaaacctgac    2820
ggctatgatt actatgcctt ttctaaagat caatactata acattgatgt gcctagtaga    2880
acagcaagag caattactac tcgttctggg cagaccttat ccaaagtctg gtacaactgt    2940
ccttaa                                                               2946
```

<210> SEQ ID NO 7
<211> LENGTH: 981
<212> TYPE: PRT
<213> ORGANISM: Artificial Sequence
<220> FEATURE:
<223> OTHER INFORMATION: Amino acid sequence of entire PRG4-LUB:1 protein.

<400> SEQUENCE: 7

```
Met Ala Trp Lys Thr Leu Pro Ile Tyr Leu Leu Leu Leu Ser Val
 1               5                  10                  15

Phe Val Ile Gln Gln Val Ser Ser Gln Asp Leu Ser Ser Cys Ala Gly
                20                  25                  30

Arg Cys Gly Glu Gly Tyr Ser Arg Asp Ala Thr Cys Asn Cys Asp Tyr
            35                  40                  45

Asn Cys Gln His Tyr Met Glu Cys Cys Pro Asp Phe Lys Arg Val Cys
    50                  55                  60

Thr Ala Glu Leu Ser Cys Lys Gly Arg Cys Phe Glu Ser Phe Glu Arg
65                  70                  75                  80

Gly Arg Glu Cys Asp Cys Asp Ala Gln Cys Lys Lys Tyr Asp Lys Cys
                85                  90                  95

Cys Pro Asp Tyr Glu Ser Phe Cys Ala Glu Val His Asn Pro Thr Ser
            100                 105                 110

Pro Pro Ser Ser Lys Lys Ala Pro Pro Ser Gly Ala Ser Gln Thr
        115                 120                 125

Ile Lys Ser Thr Thr Lys Arg Ser Pro Lys Pro Asn Lys Lys Lys
    130                 135                 140

Thr Lys Lys Val Ile Glu Ser Glu Glu Ile Thr Glu Glu His Ser Val
145                 150                 155                 160

Ser Glu Asn Gln Glu Ser Ser Ser Ser Ser Ser Ser Ser Ser Ser
                165                 170                 175

Ser Thr Ile Trp Lys Ile Lys Ser Ser Lys Asn Ser Ala Ala Asn Arg
            180                 185                 190

Glu Leu Gln Lys Lys Leu Lys Val Lys Asp Asn Lys Lys Asn Arg Thr
        195                 200                 205

Lys Lys Lys Pro Thr Pro Lys Pro Pro Val Val Asp Glu Ala Gly Ser
    210                 215                 220

Gly Leu Asp Asn Gly Asp Phe Lys Val Thr Thr Pro Asp Thr Ser Thr
225                 230                 235                 240

Thr Gln His Asn Lys Val Ser Thr Ser Pro Lys Ile Thr Thr Ala Lys
                245                 250                 255

Pro Ile Asn Pro Arg Pro Ser Leu Pro Pro Asn Ser Asp Thr Ser Lys
            260                 265                 270

Glu Thr Ser Leu Thr Val Asn Lys Glu Thr Thr Val Glu Thr Lys Glu
        275                 280                 285

Thr Thr Thr Thr Asn Lys Gln Thr Ser Thr Asp Gly Lys Glu Lys Thr
    290                 295                 300

Thr Ser Ala Lys Glu Thr Gln Ser Ile Glu Lys Thr Ser Ala Lys Asp
305                 310                 315                 320
```

```
                                -continued

Leu Ala Pro Thr Ser Lys Val Leu Ala Lys Pro Thr Pro Lys Ala Glu
                325                 330                 335

Thr Thr Thr Lys Gly Pro Ala Leu Thr Thr Pro Lys Glu Pro Thr Pro
            340                 345                 350

Thr Thr Pro Lys Glu Pro Ala Ser Thr Thr Pro Lys Glu Pro Thr Pro
        355                 360                 365

Thr Thr Ile Lys Ser Ala Pro Thr Thr Pro Lys Glu Pro Ala Pro Thr
    370                 375                 380

Thr Thr Lys Ser Ala Pro Thr Thr Pro Lys Glu Pro Ala Pro Thr Thr
385                 390                 395                 400

Thr Lys Glu Pro Ala Pro Thr Thr Pro Lys Glu Pro Ala Pro Thr Thr
                405                 410                 415

Thr Lys Pro Ala Pro Thr Thr Pro Glu Thr Pro Pro Pro Thr Thr Ser
            420                 425                 430

Glu Val Ser Thr Pro Thr Thr Thr Lys Glu Pro Thr Thr Ile His Lys
        435                 440                 445

Ser Pro Asp Glu Ser Thr Pro Glu Leu Ser Ala Glu Pro Thr Pro Lys
    450                 455                 460

Ala Leu Glu Asn Ser Pro Lys Glu Pro Gly Val Pro Thr Thr Lys Thr
465                 470                 475                 480

Pro Ala Ala Thr Lys Pro Glu Met Thr Thr Ala Lys Asp Lys Thr
                485                 490                 495

Thr Glu Arg Asp Leu Arg Thr Thr Pro Glu Thr Thr Thr Ala Ala Pro
            500                 505                 510

Lys Met Thr Lys Glu Thr Ala Thr Thr Thr Glu Lys Thr Thr Glu Ser
        515                 520                 525

Lys Ile Thr Ala Thr Thr Thr Gln Val Thr Ser Thr Thr Thr Gln Asp
    530                 535                 540

Thr Thr Pro Phe Lys Ile Thr Thr Leu Lys Thr Thr Thr Leu Ala Pro
545                 550                 555                 560

Lys Val Thr Thr Thr Lys Lys Thr Ile Thr Thr Thr Glu Ile Met Asn
                565                 570                 575

Lys Pro Glu Glu Thr Ala Lys Pro Lys Asp Arg Ala Thr Asn Ser Lys
            580                 585                 590

Ala Thr Thr Pro Lys Pro Gln Lys Pro Thr Lys Ala Pro Lys Lys Pro
        595                 600                 605

Thr Ser Thr Lys Lys Pro Lys Thr Met Pro Arg Val Arg Lys Pro Lys
    610                 615                 620

Thr Thr Pro Thr Pro Arg Lys Met Thr Ser Thr Met Pro Glu Leu Asn
625                 630                 635                 640

Pro Thr Ser Arg Ile Ala Glu Ala Met Leu Gln Thr Thr Thr Arg Pro
                645                 650                 655

Asn Gln Thr Pro Asn Ser Lys Leu Val Glu Val Asn Pro Lys Ser Glu
            660                 665                 670

Asp Ala Gly Gly Ala Glu Gly Glu Thr Pro His Met Leu Leu Arg Pro
        675                 680                 685

His Val Phe Met Pro Glu Val Thr Pro Asp Met Asp Tyr Leu Pro Arg
    690                 695                 700

Val Pro Asn Gln Gly Ile Ile Ile Asn Pro Met Leu Ser Asp Glu Thr
705                 710                 715                 720

Asn Ile Cys Asn Gly Lys Pro Val Asp Gly Leu Thr Thr Leu Arg Asn
                725                 730                 735
```

```
Gly Thr Leu Val Ala Phe Arg Gly His Tyr Phe Trp Met Leu Ser Pro
                740                 745                 750

Phe Ser Pro Ser Pro Ala Arg Arg Ile Thr Glu Val Trp Gly Ile
            755                 760                 765

Pro Ser Pro Ile Asp Thr Val Phe Thr Arg Cys Asn Cys Glu Gly Lys
        770                 775                 780

Thr Phe Phe Phe Lys Asp Ser Gln Tyr Trp Arg Phe Thr Asn Asp Ile
785                 790                 795                 800

Lys Asp Ala Gly Tyr Pro Lys Pro Ile Phe Lys Gly Phe Gly Gly Leu
                805                 810                 815

Thr Gly Gln Ile Val Ala Ala Leu Ser Thr Ala Lys Tyr Lys Asn Trp
                820                 825                 830

Pro Glu Ser Val Tyr Phe Phe Lys Arg Gly Gly Ser Ile Gln Gln Tyr
                835                 840                 845

Ile Tyr Lys Gln Glu Pro Val Gln Lys Cys Pro Gly Arg Arg Pro Ala
                850                 855                 860

Leu Asn Tyr Pro Val Tyr Gly Glu Met Thr Gln Val Arg Arg Arg Arg
865                 870                 875                 880

Phe Glu Arg Ala Ile Gly Pro Ser Gln Thr His Thr Ile Arg Ile Gln
                885                 890                 895

Tyr Ser Pro Ala Arg Leu Ala Tyr Gln Asp Lys Gly Val Leu His Asn
                900                 905                 910

Glu Val Lys Val Ser Ile Leu Trp Arg Gly Leu Pro Asn Val Val Thr
                915                 920                 925

Ser Ala Ile Ser Leu Pro Asn Ile Arg Lys Pro Asp Gly Tyr Asp Tyr
                930                 935                 940

Tyr Ala Phe Ser Lys Asp Gln Tyr Tyr Asn Ile Asp Val Pro Ser Arg
945                 950                 955                 960

Thr Ala Arg Ala Ile Thr Thr Arg Ser Gly Gln Thr Leu Ser Lys Val
                965                 970                 975

Trp Tyr Asn Cys Pro
                980

<210> SEQ ID NO 8
<211> LENGTH: 157
<212> TYPE: DNA
<213> ORGANISM: Artificial Sequence
<220> FEATURE:
<223> OTHER INFORMATION: Lub:1 DNA insert from synthetic cDNA
      cassette-1.

<400> SEQUENCE: 8
gcgcgcccac aactccaaaa gagcccgcac ctaccacgac aaagtcagct cctactacgc      60
ccaaagagcc agcgccgacg actactaaag aaccggcacc caccacgcct aaggagccag     120
ctcctactac aacgaaaccg gcaccaacca ctccgga                              157

<210> SEQ ID NO 9
<211> LENGTH: 51
<212> TYPE: PRT
<213> ORGANISM: Artificial Sequence
<220> FEATURE:
<223> OTHER INFORMATION: 51 amino acids encoded by Lub:1 DNA insert (4
      KEPAPTT sequences between S373 to E425 in SEQ ID NO: 7).

<400> SEQUENCE: 9

Ala Pro Thr Thr Pro Lys Glu Pro Ala Pro Thr Thr Lys Ser Ala
1               5                   10                  15
```

```
Pro Thr Thr Pro Lys Glu Pro Ala Pro Thr Thr Thr Lys Glu Pro Ala
            20                  25                  30

Pro Thr Thr Pro Lys Glu Pro Ala Pro Thr Thr Thr Lys Pro Ala Pro
            35                  40                  45

Thr Thr Pro
    50

<210> SEQ ID NO 10
<211> LENGTH: 3024
<212> TYPE: DNA
<213> ORGANISM: Artificial Sequence
<220> FEATURE:
<223> OTHER INFORMATION: Recombinant PRG4-Lub:2 cDNA construct.

<400> SEQUENCE: 10
atggcatgga aaacacttcc catttacctg ttgttgctgc tgtctgtttt cgtgattcag      60
caagtttcat ctcaagattt atcaagctgt gcagggagat gtggggaagg gtattctaga    120
gatgccacct gcaactgtga ttataactgt caacactaca tggagtgctg ccctgatttc    180
aagagagtct gcactgcgga gctttcctgt aaaggccgct gctttgagtc cttcgagaga    240
gggagggagt gtgactgcga cgcccaatgt aagaagtatg acaagtgctg tcccgattat    300
gagagtttct gtgcagaagt gcataatccc acatcaccac catcttcaaa gaaagcacct    360
ccaccttcag gagcatctca aaccatcaaa tcaacaacca acgttcacc caaaccacca    420 aacaagaaga agactaagaa agttatagaa tcagaggaaa taacagaaga acattctgtt    480
tctgaaaatc aagagtcctc ctccagtagc agttcaagta gttcgtcgtc gacaatttgg    540
aaaatcaagt cttccaaaaa ttcagctgct aatagagaat tacagaagaa actcaaagta    600
aaagataaca agaagaacag aactaaaaag aaacctaccc ccaaaccacc agttgtagat    660
gaagctggaa gtggattgga caatggtgac ttcaaggtca caactcctga cacgtctacc    720
acccaacaca taaagtcag cacatctccc aagatcacaa cagcaaaacc aataaatccc    780
agacccagtc ttccacctaa ttctgataca tctaaagaga cgtctttgac agtgaataaa    840
gagacaacag ttgaaactaa agaaactact acaacaaata acagacttc aactgatgga    900 aagagaagaa ctacttccgc taaagagaca caaagtatag agaaaacatc tgctaaagat    960
ttagcaccca catctaaagt gctggctaaa cctacaccca agctgaaaac tacaaccaaa   1020
ggccctgctc tcaccactcc caaggagccc acgcccacca ctcccaagga gcctgcatct   1080
accacaccca aagagcccac acctaccacc atcaagagcg cgcccacaac tccaaaagag   1140
cccgcaccta ccacgacaaa gtcagctcct actacgccca agagccagc gccgacgact   1200 actaaagaac cggcacccac cacgcctaaa gaaccagccc ctactacgac aaaggagcct   1260
gcacccacaa ccacgaagag cgcacccaca acaccaaagg agccggcccc tacgactcct   1320
aaggaaccca accggcacc aaccactccg gaaacacctc ctccaaccac ttcagaggtc   1380
tctactccaa ctaccaccaa ggagcctacc actatccaca aaagccctga tgaatcaact   1440
cctgagcttt ctgcagaacc cacaccaaaa gctcttgaaa cagtcccaa ggaacctggt   1500 gtacctacaa ctaagacgcc ggcggcgact aaacctgaaa tgactacaac agctaaagac   1560
aagacaacag aaagagactt acgtactaca cctgaaacta caactgctgc acctaagatg   1620
acaaaagaga cagcaactac aacagaaaaa actaccgaat ccaaaataac agctacaacc   1680
acacaagtaa catctaccac aactcaagat accacaccat tcaaaattac tactcttaaa   1740
acaactactc ttgcacccaa agtaactaca acaaaaaaga caattactac cactgagatt   1800
```

-continued

```
atgaacaaac ctgaagaaac agctaaacca aaagacagag ctactaattc taaagcgaca    1860
actcctaaac ctcaaaagcc aaccaaagca cccaaaaaac ccacttctac caaaaagcca    1920
aaaacaatgc ctagagtgag aaaaccaaag acgacaccaa ctccccgcaa gatgacatca    1980
acaatgccag aattgaaccc tacctcaaga atagcagaag ccatgctcca aaccaccacc    2040
agacctaacc aaactccaaa ctccaaacta gttgaagtaa atccaaagag tgaagatgca    2100
ggtggtgctg aaggagaaac acctcatatg cttctcaggc cccatgtgtt catgcctgaa    2160
gttactcccg acatggatta cttaccgaga gtacccaatc aaggcattat catcaatccc    2220
atgctttccg atgagaccaa tatatgcaat ggtaagccag tagatggact gactactttg    2280
cgcaatggga cattagttgc attccgaggt cattatttct ggatgctaag tccattcagt    2340
ccaccatctc cagctcgcag aattactgaa gtttggggta ttccttcccc cattgatact    2400
gttttactaa ggtgcaactg tgaaggaaaa actttcttct ttaaggattc tcagtactgg    2460
cgttttacca atgatataaa agatgcaggg taccccaaac caattttcaa aggatttgga    2520
ggactaactg gacaaatagt ggcagcgctt tcaacagcta aatataagaa ctggcctgaa    2580
tctgtgtatt ttttcaagag aggtggcagc attcagcagt atatttataa acaggaacct    2640
gtacagaagt gccctggaag aaggcctgct ctaaattatc cagtgtatgg agaaatgaca    2700
caggttagga gacgtcgctt tgaacgtgct ataggaccct ctcaaacaca ccatcaga     2760
attcaatatt cacctgccag actggcttat caagacaaag gtgtccttca taatgaagtt    2820
aaagtgagta tactgtggag aggacttcca aatgtggtta cctcagctat atcactgccc    2880
aacatcagaa aacctgacgg ctatgattac tatgcctttt ctaaagatca atactataac    2940
attgatgtgc ctagtagaac agcaagagca attactactc gttctgggca gaccttatcc    3000
aaagtctggt acaactgtcc ttaa                                          3024
```

<210> SEQ ID NO 11
<211> LENGTH: 1007
<212> TYPE: PRT
<213> ORGANISM: Artificial Sequence
<220> FEATURE:
<223> OTHER INFORMATION: Amino acid sequence of entire PRG4-LUB:2
      protein.

<400> SEQUENCE: 11

```
Met Ala Trp Lys Thr Leu Pro Ile Tyr Leu Leu Leu Leu Leu Ser Val
1               5                   10                  15

Phe Val Ile Gln Gln Val Ser Ser Gln Asp Leu Ser Ser Cys Ala Gly
            20                  25                  30

Arg Cys Gly Glu Gly Tyr Ser Arg Asp Ala Thr Cys Asn Cys Asp Tyr
        35                  40                  45

Asn Cys Gln His Tyr Met Glu Cys Cys Pro Asp Phe Lys Arg Val Cys
    50                  55                  60

Thr Ala Glu Leu Ser Cys Lys Gly Arg Cys Phe Glu Ser Phe Glu Arg
65                  70                  75                  80

Gly Arg Glu Cys Asp Cys Asp Ala Gln Cys Lys Lys Tyr Asp Lys Cys
                85                  90                  95

Cys Pro Asp Tyr Glu Ser Phe Cys Ala Glu Val His Asn Pro Thr Ser
            100                 105                 110

Pro Pro Ser Ser Lys Lys Ala Pro Pro Ser Gly Ala Ser Gln Thr
        115                 120                 125

Ile Lys Ser Thr Thr Lys Arg Ser Pro Lys Pro Asn Lys Lys
    130                 135                 140
```

-continued

```
Thr Lys Lys Val Ile Glu Ser Glu Glu Ile Thr Glu His Ser Val
145                 150                 155                 160

Ser Glu Asn Gln Glu Ser Ser Ser Ser Ser Ser Ser Ser Ser Ser
            165                 170                 175

Ser Thr Ile Trp Lys Ile Lys Ser Ser Lys Asn Ser Ala Ala Asn Arg
            180                 185                 190

Glu Leu Gln Lys Lys Leu Lys Val Lys Asp Asn Lys Lys Asn Arg Thr
            195                 200                 205

Lys Lys Lys Pro Thr Pro Lys Pro Pro Val Val Asp Glu Ala Gly Ser
210                 215                 220

Gly Leu Asp Asn Gly Asp Phe Lys Val Thr Thr Pro Asp Thr Ser Thr
225                 230                 235                 240

Thr Gln His Asn Lys Val Ser Thr Ser Pro Lys Ile Thr Thr Ala Lys
                245                 250                 255

Pro Ile Asn Pro Arg Pro Ser Leu Pro Pro Asn Ser Asp Thr Ser Lys
                260                 265                 270

Glu Thr Ser Leu Thr Val Asn Lys Glu Thr Thr Val Glu Thr Lys Glu
            275                 280                 285

Thr Thr Thr Thr Asn Lys Gln Thr Ser Thr Asp Gly Lys Glu Lys Thr
            290                 295                 300

Thr Ser Ala Lys Glu Thr Gln Ser Ile Glu Lys Thr Ser Ala Lys Asp
305                 310                 315                 320

Leu Ala Pro Thr Ser Lys Val Leu Ala Lys Pro Thr Pro Lys Ala Glu
                325                 330                 335

Thr Thr Thr Lys Gly Pro Ala Leu Thr Thr Pro Lys Glu Pro Thr Pro
                340                 345                 350

Thr Thr Pro Lys Glu Pro Ala Ser Thr Thr Pro Lys Glu Pro Thr Pro
                355                 360                 365

Thr Thr Ile Lys Ser Ala Pro Thr Thr Pro Lys Glu Pro Ala Pro Thr
                370                 375                 380

Thr Thr Lys Ser Ala Pro Thr Thr Pro Lys Glu Pro Ala Pro Thr Thr
385                 390                 395                 400

Thr Lys Glu Pro Ala Pro Thr Thr Pro Lys Glu Pro Ala Pro Thr Thr
                405                 410                 415

Thr Lys Glu Pro Ala Pro Thr Thr Thr Lys Ser Ala Pro Thr Thr Pro
                420                 425                 430

Lys Glu Pro Ala Pro Thr Thr Pro Lys Glu Pro Lys Pro Ala Pro Thr
                435                 440                 445

Thr Pro Glu Thr Pro Pro Thr Thr Ser Glu Val Ser Thr Pro Thr
                450                 455                 460

Thr Thr Lys Glu Pro Thr Thr Ile His Lys Ser Pro Asp Glu Ser Thr
465                 470                 475                 480

Pro Glu Leu Ser Ala Glu Pro Thr Pro Lys Ala Leu Glu Asn Ser Pro
                485                 490                 495

Lys Glu Pro Gly Val Pro Thr Thr Lys Thr Pro Ala Ala Thr Lys Pro
                500                 505                 510

Glu Met Thr Thr Thr Ala Lys Asp Lys Thr Thr Glu Arg Asp Leu Arg
        515                 520                 525

Thr Thr Pro Glu Thr Thr Thr Ala Ala Pro Lys Met Thr Lys Glu Thr
            530                 535                 540

Ala Thr Thr Thr Glu Lys Thr Thr Glu Ser Lys Ile Thr Ala Thr Thr
545                 550                 555                 560
```

-continued

```
Thr Gln Val Thr Ser Thr Thr Thr Gln Asp Thr Thr Pro Phe Lys Ile
                565                 570                 575

Thr Thr Leu Lys Thr Thr Thr Leu Ala Pro Lys Val Thr Thr Thr Lys
            580                 585                 590

Lys Thr Ile Thr Thr Thr Glu Ile Met Asn Lys Pro Glu Glu Thr Ala
        595                 600                 605

Lys Pro Lys Asp Arg Ala Thr Asn Ser Lys Ala Thr Thr Pro Lys Pro
    610                 615                 620

Gln Lys Pro Thr Lys Ala Pro Lys Lys Pro Thr Ser Thr Lys Lys Pro
625                 630                 635                 640

Lys Thr Met Pro Arg Val Arg Pro Lys Thr Thr Pro Thr Pro Arg
                645                 650                 655

Lys Met Thr Ser Thr Met Pro Glu Leu Asn Pro Thr Ser Arg Ile Ala
                660                 665                 670

Glu Ala Met Leu Gln Thr Thr Arg Pro Asn Gln Thr Pro Asn Ser
                675                 680                 685

Lys Leu Val Glu Val Asn Pro Lys Ser Glu Asp Ala Gly Gly Ala Glu
            690                 695                 700

Gly Glu Thr Pro His Met Leu Leu Arg Pro His Val Phe Met Pro Glu
705                 710                 715                 720

Val Thr Pro Asp Met Asp Tyr Leu Pro Arg Val Pro Asn Gln Gly Ile
                725                 730                 735

Ile Ile Asn Pro Met Leu Ser Asp Glu Thr Asn Ile Cys Asn Gly Lys
                740                 745                 750

Pro Val Asp Gly Leu Thr Thr Leu Arg Asn Gly Thr Leu Val Ala Phe
            755                 760                 765

Arg Gly His Tyr Phe Trp Met Leu Ser Pro Phe Ser Pro Pro Ser Pro
                770                 775                 780

Ala Arg Arg Ile Thr Glu Val Trp Gly Ile Pro Ser Pro Ile Asp Thr
785                 790                 795                 800

Val Phe Thr Arg Cys Asn Cys Glu Gly Lys Thr Phe Phe Phe Lys Asp
                805                 810                 815

Ser Gln Tyr Trp Arg Phe Thr Asn Asp Ile Lys Asp Ala Gly Tyr Pro
                820                 825                 830

Lys Pro Ile Phe Lys Gly Phe Gly Gly Leu Thr Gly Gln Ile Val Ala
            835                 840                 845

Ala Leu Ser Thr Ala Lys Tyr Lys Asn Trp Pro Glu Ser Val Tyr Phe
    850                 855                 860

Phe Lys Arg Gly Gly Ser Ile Gln Gln Tyr Ile Tyr Lys Gln Glu Pro
865                 870                 875                 880

Val Gln Lys Cys Pro Gly Arg Arg Pro Ala Leu Asn Tyr Pro Val Tyr
                885                 890                 895

Gly Glu Met Thr Gln Val Arg Arg Arg Phe Glu Arg Ala Ile Gly
                900                 905                 910

Pro Ser Gln Thr His Thr Ile Arg Ile Gln Tyr Ser Pro Ala Arg Leu
            915                 920                 925

Ala Tyr Gln Asp Lys Gly Val Leu His Asn Glu Val Lys Val Ser Ile
    930                 935                 940

Leu Trp Arg Gly Leu Pro Asn Val Val Thr Ser Ala Ile Ser Leu Pro
945                 950                 955                 960

Asn Ile Arg Lys Pro Asp Gly Tyr Asp Tyr Tyr Ala Phe Ser Lys Asp
                965                 970                 975

Gln Tyr Tyr Asn Ile Asp Val Pro Ser Arg Thr Ala Arg Ala Ile Thr
```

```
                980              985              990
Thr Arg Ser Gly Gln Thr Leu Ser Lys Val Trp Tyr Asn Cys Pro
       995             1000             1005

<210> SEQ ID NO 12
<211> LENGTH: 235
<212> TYPE: DNA
<213> ORGANISM: Artificial Sequence
<220> FEATURE:
<223> OTHER INFORMATION: Lub:2 DNA insert from synthetic cDNA cassette-1
      and one synthetic cDNA cassette-2 sequence.

<400> SEQUENCE: 12
gcgcgcccac aactccaaaa gagcccgcac ctaccacgac aaagtcagct cctactacgc      60
ccaaagagcc agcgccgacg actactaaag aaccggcacc caccacgcct aaagaaccag     120 ccccctactac gacaaaggag cctgcaccca caaccacgaa gagcgcaccc acaacaccaa    180
aggagccggc ccctacgact cctaaggaac ccaaaccggc accaaccact ccgga          235

<210> SEQ ID NO 13
<211> LENGTH: 77
<212> TYPE: PRT
<213> ORGANISM: Artificial Sequence
<220> FEATURE:
<223> OTHER INFORMATION: 77 amino acids encoded by Lub:2 DNA insert (6
      KEPAPTT sequences between S373 and E451 in SEQ ID NO: 11).

<400> SEQUENCE: 13

Ala Pro Thr Thr Pro Lys Glu Pro Ala Pro Thr Thr Lys Ser Ala
1               5                  10                  15

Pro Thr Thr Pro Lys Glu Pro Ala Pro Thr Thr Lys Glu Pro Ala
            20                  25                  30

Pro Thr Thr Pro Lys Glu Pro Ala Pro Thr Thr Lys Glu Pro Ala
        35                  40                  45

Pro Thr Thr Lys Ser Ala Pro Thr Thr Pro Lys Glu Pro Ala Pro
    50                  55                  60

Thr Thr Pro Lys Glu Pro Lys Pro Ala Pro Thr Thr Pro
65                  70                  75

<210> SEQ ID NO 14
<211> LENGTH: 3117
<212> TYPE: DNA
<213> ORGANISM: Artificial Sequence
<220> FEATURE:
<223> OTHER INFORMATION: Recombinant PRG4-Lub:3 cDNA construct.

<400> SEQUENCE: 14
atggcatgga aaacacttcc catttacctg ttgttgctgc tgtctgtttt cgtgattcag       60
caagtttcat ctcaagattt atcaagctgt gcagggagat gtggggaagg gtattctaga     120
gatgccacct gcaactgtga ttataactgt caacactaca tggagtgctg ccctgatttc     180
aagagagtct gcactgcgga gctttcctgt aaaggccgct gctttgagtc cttcgagaga     240
gggagggagt gtgactgcga cgcccaatgt aagaagtatg acaagtgctg tcccgattat     300
gagagttttc gtgcagaagt gcataatccc acatcaccac catcttcaaa gaaagcacct     360
ccaccttcag gagcatctca aaccatcaaa tcaacaacca acgttcacc caaaccacca      420 aacaagaaga agactaagaa agttatagaa tcagaggaaa taacagaaga acattctgtt     480
tctgaaaatc aagagtcctc ctccagtagc agttcaagta gttcgtcgtc gacaatttgg     540
aaaatcaagt cttccaaaaa ttcagctgct aatagagaat acagaagaa actcaaagta     600
```

-continued

```
aaagataaca agaagaacag aactaaaaag aaacctaccc ccaaaccacc agttgtagat      660
gaagctggaa gtggattgga caatggtgac ttcaaggtca caactcctga cacgtctacc      720
acccaacaca ataaagtcag cacatctccc aagatcacaa cagcaaaacc aataaatccc      780
agacccagtc ttccacctaa ttctgataca tctaaagaga cgtctttgac agtgaataaa      840
gagacaacag ttgaaactaa agaaactact acaacaaata aacagacttc aactgatgga      900
aaagagaaga ctacttccgc taaagagaca caaagtatag agaaaacatc tgctaaagat      960
ttagcaccca catctaaagt gctggctaaa cctacaccca agctgaaaac tacaaccaaa     1020
ggccctgctc tcaccactcc caaggagccc acgcccacca ctcccaagga gcctgcatct     1080
accacaccca aagagcccac acctaccacc atcaagagcg cgcccacaac tccaaaagag     1140
cccgcaccta ccacgacaaa gtcagctcct actacgccca aagagccagc gccgacgact     1200
actaaagaac cggcacccac cacgcctaaa gaaccagccc ctactacgac aaaggagcct     1260
gcacccacaa ccacgaagag cgcacccaca acaccaaagg agccggcccc tacgactcct     1320
aaagaaccag cccctactac gacaaaggag cctgcaccca caaccacgaa gagcgcaccc     1380
acaacaccaa aggagccggc ccctacgact cctaaggaac ccaaaccggc accaaccact     1440
ccggaaacac ctcctccaac cacttcagag gtctctactc caactaccac caaggagcct     1500
accactatcc acaaaagccc tgatgaatca actcctgagc tttctgcaga acccacacca     1560
aaagctcttg aaaacagtcc caaggaacct ggtgtaccta caactaagac gccggcggcg     1620
actaaacctg aaatgactac aacagctaaa gacaagacaa cagaaagaga cttacgtact     1680
acacctgaaa ctacaactgc tgcacctaag atgacaaaag agacagcaac tacaacagaa     1740
aaaactaccg aatccaaaat aacagctaca accacacaag taacatctac cacaactcaa     1800
gataccacac cattcaaaat tactactctt aaaacaacta ctcttgcacc caaagtaact     1860
acaacaaaaa agacaattac taccactgag attatgaaca aacctgaaga acagctaaa      1920
ccaaaagaca gagctactaa ttctaaagcg acaactccta aacctcaaaa gccaaccaaa     1980
gcacccaaaa aacccacttc taccaaaaag ccaaaaacaa tgcctagagt gagaaaacca     2040
aagacgacac caactccccg caagatgaca tcaacaatgc cagaattgaa ccctacctca     2100
agaatagcag aagccatgct ccaaaccacc accagaccta accaaactcc aaactccaaa     2160
ctagttgaag taaatccaaa gagtgaagat gcaggtggtg ctgaaggaga aacacctcat     2220
atgcttctca ggccccatgt gttcatgcct gaagttactc ccgacatgga ttacttaccg     2280
agagtaccca atcaaggcat tatcatcaat cccatgcttt ccgatgagac caatatatgc     2340
aatggtaagc cagtagatgg actgactact ttgcgcaatg ggacattagt tgcattccga     2400
ggtcattatt tctggatgct aagtccattc agtccaccat ctccagctcg cagaattact     2460
gaagtttggg gtattccttc ccccattgat actgttttta ctaggtgcaa ctgtgaagga     2520
aaaactttct tctttaagga ttctcagtac tggcgtttta ccaatgatat aaaagatgca     2580
gggtacccca aaccaatttt caaaggattt ggaggactaa ctggacaaat agtggcagcg     2640
cttttcaacag ctaaatataa gaactggcct gaatctgtgt attttttcaa gagaggtggc     2700
agcattcagc agtatatttta taaacaggaa cctgtacaga agtgccctgg aagaaggcct     2760
gctctaaatt atccagtgta tggagaaatg acacaggtta ggagacgtcg ctttgaacgt     2820
gctataggac cttctcaaac acacaccatc agaattcaat attcacctgc agactggct      2880
tatcaagaca aaggtgtcct tcataatgaa gttaaagtga gtatactgtg gagaggactt     2940
```

```
ccaaatgtgg ttacctcagc tatatcactg cccaacatca gaaaacctga cggctatgat    3000
tactatgcct tttctaaaga tcaatactat aacattgatg tgcctagtag aacagcaaga    3060
gcaattacta ctcgttctgg gcagaccta tccaaagtct ggtacaactg tccttaa       3117
```

<210> SEQ ID NO 15
<211> LENGTH: 1038
<212> TYPE: PRT
<213> ORGANISM: Artificial Sequence
<220> FEATURE:
<223> OTHER INFORMATION: amino acid sequence of entire PRG4-LUB:3 protein

<400> SEQUENCE: 15

```
Met Ala Trp Lys Thr Leu Pro Ile Tyr Leu Leu Leu Leu Ser Val
1               5                   10                  15

Phe Val Ile Gln Gln Val Ser Ser Gln Asp Leu Ser Ser Cys Ala Gly
            20                  25                  30

Arg Cys Gly Glu Gly Tyr Ser Arg Asp Ala Thr Cys Asn Cys Asp Tyr
        35                  40                  45

Asn Cys Gln His Tyr Met Glu Cys Cys Pro Asp Phe Lys Arg Val Cys
    50                  55                  60

Thr Ala Glu Leu Ser Cys Lys Gly Arg Cys Phe Glu Ser Phe Glu Arg
65                  70                  75                  80

Gly Arg Glu Cys Asp Cys Asp Ala Gln Cys Lys Lys Tyr Asp Lys Cys
                85                  90                  95

Cys Pro Asp Tyr Glu Ser Phe Cys Ala Glu Val His Asn Pro Thr Ser
            100                 105                 110

Pro Pro Ser Ser Lys Lys Ala Pro Pro Ser Gly Ala Ser Gln Thr
        115                 120                 125

Ile Lys Ser Thr Thr Lys Arg Ser Pro Lys Pro Pro Asn Lys Lys Lys
    130                 135                 140

Thr Lys Lys Val Ile Glu Ser Glu Glu Ile Thr Glu Glu His Ser Val
145                 150                 155                 160

Ser Glu Asn Gln Glu Ser Ser Ser Ser Ser Ser Ser Ser Ser Ser
                165                 170                 175

Ser Thr Ile Trp Lys Ile Lys Ser Ser Lys Asn Ser Ala Ala Asn Arg
            180                 185                 190

Glu Leu Gln Lys Lys Leu Lys Val Lys Asp Asn Lys Lys Asn Arg Thr
        195                 200                 205

Lys Lys Lys Pro Thr Pro Lys Pro Pro Val Val Asp Glu Ala Gly Ser
    210                 215                 220

Gly Leu Asp Asn Gly Asp Phe Lys Val Thr Thr Pro Asp Thr Ser Thr
225                 230                 235                 240

Thr Gln His Asn Lys Val Ser Thr Ser Pro Lys Ile Thr Thr Ala Lys
                245                 250                 255

Pro Ile Asn Pro Arg Pro Ser Leu Pro Pro Asn Ser Asp Thr Ser Lys
            260                 265                 270

Glu Thr Ser Leu Thr Val Asn Lys Glu Thr Thr Val Glu Thr Lys Glu
        275                 280                 285

Thr Thr Thr Thr Asn Lys Gln Thr Ser Thr Asp Gly Lys Glu Lys Thr
    290                 295                 300

Thr Ser Ala Lys Glu Thr Gln Ser Ile Glu Lys Thr Ser Ala Lys Asp
305                 310                 315                 320

Leu Ala Pro Thr Ser Lys Val Leu Ala Lys Pro Thr Pro Lys Ala Glu
                325                 330                 335
```

```
Thr Thr Thr Lys Gly Pro Ala Leu Thr Thr Pro Lys Glu Pro Thr Pro
            340                 345                 350
Thr Thr Pro Lys Glu Pro Ala Ser Thr Thr Pro Lys Glu Pro Thr Pro
            355                 360                 365
Thr Thr Ile Lys Ser Ala Pro Thr Thr Pro Lys Glu Pro Ala Pro Thr
            370                 375                 380
Thr Thr Lys Ser Ala Pro Thr Thr Pro Lys Glu Pro Ala Pro Thr Thr
385                 390                 395                 400
Thr Lys Glu Pro Ala Pro Thr Thr Pro Lys Glu Pro Ala Pro Thr Thr
                405                 410                 415
Thr Lys Glu Pro Ala Pro Thr Thr Thr Lys Ser Ala Pro Thr Thr Pro
                420                 425                 430
Lys Glu Pro Ala Pro Thr Thr Pro Lys Glu Pro Ala Pro Thr Thr Thr
            435                 440                 445
Lys Glu Pro Ala Pro Thr Thr Thr Lys Ser Ala Pro Thr Thr Pro Lys
            450                 455                 460
Glu Pro Ala Pro Thr Thr Pro Lys Glu Pro Lys Pro Ala Pro Thr Thr
465                 470                 475                 480
Pro Glu Thr Pro Pro Thr Thr Ser Glu Val Ser Thr Pro Thr Thr Thr
                485                 490                 495
Thr Lys Glu Pro Thr Thr Ile His Lys Ser Pro Asp Glu Ser Thr Pro
                500                 505                 510
Glu Leu Ser Ala Glu Pro Thr Pro Lys Ala Leu Glu Asn Ser Pro Lys
                515                 520                 525
Glu Pro Gly Val Pro Thr Thr Lys Thr Pro Ala Ala Thr Lys Pro Glu
            530                 535                 540
Met Thr Thr Thr Ala Lys Asp Lys Thr Thr Glu Arg Asp Leu Arg Thr
545                 550                 555                 560
Thr Pro Glu Thr Thr Thr Ala Ala Pro Lys Met Thr Lys Glu Thr Ala
                565                 570                 575
Thr Thr Thr Glu Lys Thr Thr Glu Ser Lys Ile Thr Ala Thr Thr Thr
                580                 585                 590
Gln Val Thr Ser Thr Thr Thr Gln Asp Thr Thr Pro Phe Lys Ile Thr
            595                 600                 605
Thr Leu Lys Thr Thr Thr Leu Ala Pro Lys Val Thr Thr Thr Lys Lys
            610                 615                 620
Thr Ile Thr Thr Thr Glu Ile Met Asn Lys Pro Glu Glu Thr Ala Lys
625                 630                 635                 640
Pro Lys Asp Arg Ala Thr Asn Ser Lys Ala Thr Thr Pro Lys Pro Gln
                645                 650                 655
Lys Pro Thr Lys Ala Pro Lys Lys Pro Thr Ser Thr Lys Lys Pro Lys
            660                 665                 670
Thr Met Pro Arg Val Arg Lys Pro Lys Thr Thr Pro Thr Pro Arg Lys
            675                 680                 685
Met Thr Ser Thr Met Pro Glu Leu Asn Pro Thr Ser Arg Ile Ala Glu
            690                 695                 700
Ala Met Leu Gln Thr Thr Thr Arg Pro Asn Gln Thr Pro Asn Ser Lys
705                 710                 715                 720
Leu Val Glu Val Asn Pro Lys Ser Glu Asp Ala Gly Gly Ala Glu Gly
                725                 730                 735
Glu Thr Pro His Met Leu Leu Arg Pro His Val Phe Met Pro Glu Val
            740                 745                 750
```

```
Thr Pro Asp Met Asp Tyr Leu Pro Arg Val Pro Asn Gln Gly Ile Ile
        755                 760                 765

Ile Asn Pro Met Leu Ser Asp Glu Thr Asn Ile Cys Asn Gly Lys Pro
    770                 775                 780

Val Asp Gly Leu Thr Thr Leu Arg Asn Gly Thr Leu Val Ala Phe Arg
785                 790                 795                 800

Gly His Tyr Phe Trp Met Leu Ser Pro Phe Ser Pro Pro Ser Pro Ala
                805                 810                 815

Arg Arg Ile Thr Glu Val Trp Gly Ile Pro Ser Pro Ile Asp Thr Val
                820                 825                 830

Phe Thr Arg Cys Asn Cys Glu Gly Lys Thr Phe Phe Lys Asp Ser
                835                 840                 845

Gln Tyr Trp Arg Phe Thr Asn Asp Ile Lys Asp Ala Gly Tyr Pro Lys
    850                 855                 860

Pro Ile Phe Lys Gly Phe Gly Gly Leu Thr Gly Gln Ile Val Ala Ala
865                 870                 875                 880

Leu Ser Thr Ala Lys Tyr Lys Asn Trp Pro Glu Ser Val Tyr Phe Phe
                885                 890                 895

Lys Arg Gly Gly Ser Ile Gln Gln Tyr Ile Tyr Lys Gln Glu Pro Val
                900                 905                 910

Gln Lys Cys Pro Gly Arg Arg Pro Ala Leu Asn Tyr Pro Val Tyr Gly
    915                 920                 925

Glu Met Thr Gln Val Arg Arg Arg Phe Glu Arg Ala Ile Gly Pro
    930                 935                 940

Ser Gln Thr His Thr Ile Arg Ile Gln Tyr Ser Pro Ala Arg Leu Ala
945                 950                 955                 960

Tyr Gln Asp Lys Gly Val Leu His Asn Glu Val Lys Val Ser Ile Leu
                965                 970                 975

Trp Arg Gly Leu Pro Asn Val Val Thr Ser Ala Ile Ser Leu Pro Asn
                980                 985                 990

Ile Arg Lys Pro Asp Gly Tyr Asp Tyr Tyr Ala Phe Ser Lys Asp Gln
    995                 1000                1005

Tyr Tyr Asn Ile Asp Val Pro Ser Arg Thr Ala Arg Ala Ile Thr
    1010                1015                1020

Thr Arg Ser Gly Gln Thr Leu Ser Lys Val Trp Tyr Asn Cys Pro
    1025                1030                1035

<210> SEQ ID NO 16
<211> LENGTH: 328
<212> TYPE: DNA
<213> ORGANISM: Artificial Sequence
<220> FEATURE:
<223> OTHER INFORMATION: Lub:3 DNA insert from synthetic cDNA cassette-1
      and two synthetic cDNA cassette-2 sequences.

<400> SEQUENCE: 16
gcgcgcccac aactccaaaa gagcccgcac ctaccacgac aaagtcagct cctactacgc      60
ccaaagagcc agcgccgacg actactaaag aaccggcacc caccacgcct aaagaaccag    120
cccctactac gacaaaggag cctgcaccca caaccacgaa gagcgcaccc acaacaccaa    180
aggagccggc ccctacgact cctaaagaac cagcccctac tacgacaaag gagcctgcac    240
ccacaaccac gaagagcgca cccacaacac caaaggagcc ggcccctacg actcctaagg    300
aacccaaacc ggcaccaacc actccgga                                        328

<210> SEQ ID NO 17
```

```
<211> LENGTH: 108
<212> TYPE: PRT
<213> ORGANISM: Artificial Sequence
<220> FEATURE:
<223> OTHER INFORMATION: 108 amino acids encoded by Lub:3 DNA insert (9
      KEPAPTT sequences between S373 and E482 in SEQ ID NO: 15)

<400> SEQUENCE: 17
```

Ala Pro Thr Thr Pro Lys Glu Pro Ala Pro Thr Thr Lys Ser Ala
1               5                   10                  15

Pro Thr Thr Pro Lys Glu Pro Ala Pro Thr Thr Thr Lys Glu Pro Ala
            20                  25                  30

Pro Thr Thr Pro Lys Glu Pro Ala Pro Thr Thr Lys Glu Pro Ala
        35                  40                  45

Pro Thr Thr Thr Lys Ser Ala Pro Thr Thr Pro Lys Glu Pro Ala Pro
    50                  55                  60

Thr Thr Pro Lys Glu Pro Ala Pro Thr Thr Lys Glu Pro Ala Pro
65                  70                  75                  80

Thr Thr Thr Lys Ser Ala Pro Thr Thr Pro Lys Glu Pro Ala Pro Thr
                85                  90                  95

Thr Pro Lys Glu Pro Lys Pro Ala Pro Thr Thr Pro
            100                 105

```
<210> SEQ ID NO 18
<211> LENGTH: 3210
<212> TYPE: DNA
<213> ORGANISM: Artificial Sequence
<220> FEATURE:
<223> OTHER INFORMATION: recombinant PRG4-Lub:4 cDNA construct.

<400> SEQUENCE: 18
```

| | | |
|---|---|---|
| atggcatgga aaacacttcc catttacctg ttgttgctgc tgtctgtttt cgtgattcag | 60 |
| caagtttcat ctcaagattt atcaagctgt gcagggagat gtggggaagg gtattctaga | 120 |
| gatgccacct gcaactgtga ttataactgt caacactaca tggagtgctg ccctgatttc | 180 |
| aagagagtct gcactgcgga gctttcctgt aaaggccgct gctttgagtc cttcgagaga | 240 |
| gggagggagt gtgactgcga cgcccaatgt aagaagtatg acaagtgctg tcccgattat | 300 |
| gagagtttct gtgcagaagt gcataatccc acatcaccac catcttcaaa gaaagcacct | 360 |
| ccaccttcag gagcatctca aaccatcaaa tcaacaacca acgttcacc caaaccacca | 420 |
| aacaagaaga agactaagaa agttatagaa tcagaggaaa taacagaaga acattctgtt | 480 |
| tctgaaaatc aagagtcctc ctccagtagc agttcaagta gttcgtcgtc gacaatttgg | 540 |
| aaaatcaagt cttccaaaaa ttcagctgct aatagagaat tacagaagaa actcaaagta | 600 |
| aaagataaca agaagaacag aactaaaaag aaacctaccc ccaaaccacc agttgtagat | 660 |
| gaagctggaa gtggattgga caatggtgac ttcaaggtca caactcctga cacgtctacc | 720 |
| acccaacaca ataaagtcag cacatctccc aagatcacaa cagcaaaacc aataaatccc | 780 |
| agacccagtc ttccacctaa ttctgataca tctaaagaga cgtctttgac agtgaataaa | 840 |
| gagacaacag ttgaaactaa agaaactact acaacaaata acagacttc aactgatgga | 900 |
| aaagagaaga ctacttccgc taaagagaca caaagtatag aaaaacatc tgctaaagat | 960 |
| ttagcacca catctaaagt gctggctaaa cctacaccca agctgaaac tacaaccaaa | 1020 |
| ggccctgctc tcaccactcc caaggagccc acgcccacca ctcccaagga gcctgcatct | 1080 |
| accacaccca aagagcccac acctaccacc atcaagagcg cgcccacaac tccaaaagag | 1140 |
| cccgcaccta ccacgacaaa gtcagctcct actacgccca aagagccagc gccgacgact | 1200 |

-continued

```
actaaagaac cggcacccac cacgcctaaa gaaccagccc ctactacgac aaaggagcct    1260
gcacccacaa ccacgaagag cgcacccaca acaccaaagg agccggcccc tacgactcct    1320
aaagaaccag cccctactac gacaaaggag cctgcaccca caaccacgaa gagcgcaccc    1380
acaacaccaa aggagccggc ccctacgact cctaagaaac cagcccctac tacgacaaag    1440
gagcctgcac ccacaaccac gaagagcgca cccacaacac caaaggagcc ggcccctacg    1500
actcctaagg aacccaaacc ggcaccaacc actccggaaa cacctcctcc aaccacttca    1560
gaggtctcta ctccaactac caccaaggag cctaccacta tccacaaaag ccctgatgaa    1620
tcaactcctg agctttctgc agaacccaca ccaaaagctc ttgaaaacag tcccaaggaa    1680
cctggtgtac ctacaactaa gacgccggcg gcgactaaac tgaaatgac tacaacagct    1740 aaagacaaga caacagaaag agacttacgt actacacctg aaactacaac tgctgcacct    1800
aagatgacaa aagagacagc aactacaaca gaaaaaacta ccgaatccaa aataacagct    1860
acaaccacac aagtaacatc taccacaact caagatacca caccattcaa aattactact    1920
cttaaaacaa ctactcttgc acccaaagta actacaacaa aaaagacaat tactaccact    1980
gagattatga caaacctga gaaacagct aaaccaaaag acagagctac taattctaaa    2040
gcgacaactc ctaaacctca aaagccaacc aaagcaccca aaaaacccac ttctaccaaa    2100
aagccaaaaa caatgcctag agtgagaaaa ccaaagacga caccaactcc ccgcaagatg    2160
acatcaacaa tgccagaatt gaaccctacc tcaagaatag cagaagccat gctccaaacc    2220
accaccagac ctaaccaaac tccaaactcc aaactagttg aagtaaatcc aaagagtgaa    2280
gatgcaggtg gtgctgaagg agaaacacct catatgcttc tcaggcccca tgtgttcatg    2340
cctgaagtta ctcccgacat ggattactta ccgagagtac ccaatcaagg cattatcatc    2400
aatcccatgc tttccgatga gaccaatata tgcaatggta agccagtaga tggactgact    2460
actttgcgca atgggacatt agttgcattc cgaggtcatt atttctggat gctaagtcca    2520
ttcagtccac catctccagc tcgcagaatt actgaagttt ggggtattcc ttcccccatt    2580
gatactgttt ttactaggtg caactgtgaa ggaaaaactt tcttctttaa ggattctcag    2640
tactggcgtt ttaccaatga tataaaagat gcagggtacc ccaaaccaat tttcaaagga    2700
tttggaggac taactggaca aatagtggca gcgctttcaa cagctaaata taagaactgg    2760
cctgaatctg tgtattttt caagagaggt ggcagcattc agcagtatat ttataaacag    2820
gaacctgtac agaagtgccc tggaagaagg cctgctctaa attatccagt gtatggagaa    2880
atgacacagg ttaggagacg tcgctttgaa cgtgctatag accttctca acacacacc    2940 atcagaattc aatattcacc tgccagactg gcttatcaag acaaaggtgt ccttcataat    3000
gaagttaaag tgagtatact gtggagagga cttccaaatg tggttacctc agctatatca    3060
ctgcccaaca tcagaaaacc tgacggctat gattactatg ccttttctaa agatcaatac    3120
tataacattg atgtgcctag tagaacagca agagcaatta ctactcgttc tgggcagacc    3180
ttatccaaag tctggtacaa ctgtccttaa                                     3210
```

<210> SEQ ID NO 19
<211> LENGTH: 1069
<212> TYPE: PRT
<213> ORGANISM: Artificial Sequence
<220> FEATURE:
<223> OTHER INFORMATION: amino acid sequence of entire PRG4-LUB:4
    protein.

<400> SEQUENCE: 19

-continued

```
Met Ala Trp Lys Thr Leu Pro Ile Tyr Leu Leu Leu Leu Ser Val
1               5                   10                  15

Phe Val Ile Gln Gln Val Ser Ser Gln Asp Leu Ser Ser Cys Ala Gly
                20                  25                  30

Arg Cys Gly Glu Gly Tyr Ser Arg Asp Ala Thr Cys Asn Cys Asp Tyr
            35                  40                  45

Asn Cys Gln His Tyr Met Glu Cys Cys Pro Asp Phe Lys Arg Val Cys
    50                  55                  60

Thr Ala Glu Leu Ser Cys Lys Gly Arg Cys Phe Glu Ser Phe Glu Arg
65                  70                  75                  80

Gly Arg Glu Cys Asp Cys Asp Ala Gln Cys Lys Lys Tyr Asp Lys Cys
                85                  90                  95

Cys Pro Asp Tyr Glu Ser Phe Cys Ala Glu Val His Asn Pro Thr Ser
            100                 105                 110

Pro Pro Ser Ser Lys Lys Ala Pro Pro Ser Gly Ala Ser Gln Thr
    115                 120                 125

Ile Lys Ser Thr Thr Lys Arg Ser Pro Lys Pro Pro Asn Lys Lys Lys
    130                 135                 140

Thr Lys Lys Val Ile Glu Ser Glu Glu Ile Thr Glu Glu His Ser Val
145                 150                 155                 160

Ser Glu Asn Gln Glu Ser Ser Ser Ser Ser Ser Ser Ser Ser Ser Ser
                165                 170                 175

Ser Thr Ile Trp Lys Ile Lys Ser Ser Lys Asn Ser Ala Ala Asn Arg
            180                 185                 190

Glu Leu Gln Lys Lys Leu Lys Val Lys Asp Asn Lys Lys Asn Arg Thr
        195                 200                 205

Lys Lys Lys Pro Thr Pro Lys Pro Pro Val Val Asp Glu Ala Gly Ser
    210                 215                 220

Gly Leu Asp Asn Gly Asp Phe Lys Val Thr Thr Pro Asp Thr Ser Thr
225                 230                 235                 240

Thr Gln His Asn Lys Val Ser Thr Ser Pro Lys Ile Thr Thr Ala Lys
                245                 250                 255

Pro Ile Asn Pro Arg Pro Ser Leu Pro Pro Asn Ser Asp Thr Ser Lys
            260                 265                 270

Glu Thr Ser Leu Thr Val Asn Lys Glu Thr Thr Val Glu Thr Lys Glu
        275                 280                 285

Thr Thr Thr Thr Asn Lys Gln Thr Ser Thr Asp Gly Lys Glu Lys Thr
    290                 295                 300

Thr Ser Ala Lys Glu Thr Gln Ser Ile Glu Lys Thr Ser Ala Lys Asp
305                 310                 315                 320

Leu Ala Pro Thr Ser Lys Val Leu Ala Lys Pro Thr Pro Lys Ala Glu
                325                 330                 335

Thr Thr Thr Lys Gly Pro Ala Leu Thr Thr Pro Lys Glu Pro Thr Pro
            340                 345                 350

Thr Thr Pro Lys Glu Pro Ala Ser Thr Thr Pro Lys Glu Pro Thr Pro
        355                 360                 365

Thr Thr Ile Lys Ser Ala Pro Thr Thr Pro Lys Glu Pro Ala Pro Thr
    370                 375                 380

Thr Thr Lys Ser Ala Pro Thr Thr Pro Lys Glu Pro Ala Pro Thr Thr
385                 390                 395                 400

Thr Lys Glu Pro Ala Pro Thr Thr Pro Lys Glu Pro Ala Pro Thr Thr
                405                 410                 415
```

```
Thr Lys Glu Pro Ala Pro Thr Thr Lys Ser Ala Pro Thr Thr Pro
            420                 425                 430

Lys Glu Pro Ala Pro Thr Thr Pro Lys Glu Pro Ala Pro Thr Thr Thr
        435                 440                 445

Lys Glu Pro Ala Pro Thr Thr Lys Ser Ala Pro Thr Thr Pro Lys
        450                 455                 460

Glu Pro Ala Pro Thr Thr Pro Lys Glu Pro Ala Pro Thr Thr Lys
465                 470                 475                 480

Glu Pro Ala Pro Thr Thr Lys Ser Ala Pro Thr Thr Pro Lys Glu
            485                 490                 495

Pro Ala Pro Thr Thr Pro Lys Glu Pro Lys Pro Ala Pro Thr Thr Pro
            500                 505                 510

Glu Thr Pro Pro Thr Thr Ser Glu Val Ser Thr Pro Thr Thr Thr
            515                 520                 525

Lys Glu Pro Thr Thr Ile His Lys Ser Pro Asp Glu Ser Thr Pro Glu
            530                 535                 540

Leu Ser Ala Glu Pro Thr Pro Lys Ala Leu Glu Asn Ser Pro Lys Glu
545                 550                 555                 560

Pro Gly Val Pro Thr Thr Lys Thr Pro Ala Ala Thr Lys Pro Glu Met
                565                 570                 575

Thr Thr Thr Ala Lys Asp Lys Thr Thr Glu Arg Asp Leu Arg Thr Thr
            580                 585                 590

Pro Glu Thr Thr Thr Ala Ala Pro Lys Met Thr Lys Glu Thr Ala Thr
            595                 600                 605

Thr Thr Glu Lys Thr Thr Glu Ser Lys Ile Thr Ala Thr Thr Thr Gln
            610                 615                 620

Val Thr Ser Thr Thr Thr Gln Asp Thr Thr Pro Phe Lys Ile Thr Thr
625                 630                 635                 640

Leu Lys Thr Thr Thr Leu Ala Pro Lys Val Thr Thr Thr Lys Lys Thr
                645                 650                 655

Ile Thr Thr Thr Glu Ile Met Asn Lys Pro Glu Glu Thr Ala Lys Pro
            660                 665                 670

Lys Asp Arg Ala Thr Asn Ser Lys Ala Thr Thr Pro Lys Pro Gln Lys
            675                 680                 685

Pro Thr Lys Ala Pro Lys Lys Pro Thr Ser Thr Lys Lys Pro Lys Thr
            690                 695                 700

Met Pro Arg Val Arg Lys Pro Lys Thr Thr Pro Thr Pro Arg Lys Met
705                 710                 715                 720

Thr Ser Thr Met Pro Glu Leu Asn Pro Thr Ser Arg Ile Ala Glu Ala
                725                 730                 735

Met Leu Gln Thr Thr Thr Arg Pro Asn Gln Thr Pro Asn Ser Lys Leu
            740                 745                 750

Val Glu Val Asn Pro Lys Ser Glu Asp Ala Gly Gly Ala Glu Gly Glu
                755                 760                 765

Thr Pro His Met Leu Leu Arg Pro His Val Phe Met Pro Glu Val Thr
            770                 775                 780

Pro Asp Met Asp Tyr Leu Pro Arg Val Pro Asn Gln Gly Ile Ile Ile
785                 790                 795                 800

Asn Pro Met Leu Ser Asp Glu Thr Asn Ile Cys Asn Gly Lys Pro Val
                805                 810                 815

Asp Gly Leu Thr Thr Leu Arg Asn Gly Thr Leu Val Ala Phe Arg Gly
            820                 825                 830

His Tyr Phe Trp Met Leu Ser Pro Phe Ser Pro Pro Ser Pro Ala Arg
```

```
                   835                 840                 845
Arg Ile Thr Glu Val Trp Gly Ile Pro Ser Pro Ile Asp Thr Val Phe
    850                 855                 860

Thr Arg Cys Asn Cys Glu Gly Lys Thr Phe Phe Phe Lys Asp Ser Gln
865                 870                 875                 880

Tyr Trp Arg Phe Thr Asn Asp Ile Lys Asp Ala Gly Tyr Pro Lys Pro
                885                 890                 895

Ile Phe Lys Gly Phe Gly Gly Leu Thr Gly Gln Ile Val Ala Ala Leu
                900                 905                 910

Ser Thr Ala Lys Tyr Lys Asn Trp Pro Glu Ser Val Tyr Phe Phe Lys
                915                 920                 925

Arg Gly Gly Ser Ile Gln Gln Tyr Ile Tyr Lys Gln Glu Pro Val Gln
    930                 935                 940

Lys Cys Pro Gly Arg Arg Pro Ala Leu Asn Tyr Pro Val Tyr Gly Glu
945                 950                 955                 960

Met Thr Gln Val Arg Arg Arg Phe Glu Arg Ala Ile Gly Pro Ser
                965                 970                 975

Gln Thr His Thr Ile Arg Ile Gln Tyr Ser Pro Ala Arg Leu Ala Tyr
                980                 985                 990

Gln Asp Lys Gly Val Leu His Asn  Glu Val Lys Val Ser  Ile Leu Trp
            995                 1000                1005

Arg Gly  Leu Pro Asn Val Val  Thr Ser Ala Ile Ser  Leu Pro Asn
    1010                1015                1020

Ile Arg  Lys Pro Asp Gly Tyr  Asp Tyr Tyr Ala Phe  Ser Lys Asp
    1025                1030                1035

Gln Tyr  Tyr Asn Ile Asp Val  Pro Ser Arg Thr Ala  Arg Ala Ile
    1040                1045                1050

Thr Thr  Arg Ser Gly Gln Thr  Leu Ser Lys Val Trp  Tyr Asn Cys
    1055                1060                1065
Pro

<210> SEQ ID NO 20
<211> LENGTH: 421
<212> TYPE: DNA
<213> ORGANISM: Artificial Sequence
<220> FEATURE:
<223> OTHER INFORMATION: Lub:4 DNA insert from cDNA cassette-1 and three
      synthetic cDNA cassette-2 sequences.

<400> SEQUENCE: 20
gcgcgcccac aactccaaaa gagcccgcac ctaccacgac aaagtcagct cctactacgc        60
ccaaagagcc agcgccgacg actactaaag aaccggcacc caccacgcct aaagaaccag       120 ccccctactac gacaaaggag cctgcaccca caaccacgaa gagcgcaccc acaacaccaa       180
aggagccggc ccctacgact cctaaagaac cagcccctac tacgacaaag gagcctgcac       240
ccacaaccac gaagagcgca cccacaacac caaaggagcc ggcccctacg actcctaaag       300
aaccagcccc tactacgaca aaggagcctg cacccacaac cacgaagagc gcacccacaa       360
caccaaagga gccggcccct acgactccta aggaacccaa accggcacca accactccgg       420
a                                                                       421

<210> SEQ ID NO 21
<211> LENGTH: 139
<212> TYPE: PRT
<213> ORGANISM: Artificial Sequence
<220> FEATURE:
```

```
<223> OTHER INFORMATION: 139 amino acids encoded by Lub:4 DNA insert (12
      KEPAPTT sequences between S373 and E513 in SEQ ID NO: 19)

<400> SEQUENCE: 21

Ala Pro Thr Thr Pro Lys Glu Pro Ala Pro Thr Thr Lys Ser Ala
1               5                   10                  15

Pro Thr Thr Pro Lys Glu Pro Ala Pro Thr Thr Thr Lys Glu Pro Ala
            20                  25                  30

Pro Thr Thr Pro Lys Glu Pro Ala Pro Thr Thr Thr Lys Glu Pro Ala
            35                  40                  45

Pro Thr Thr Thr Lys Ser Ala Pro Thr Thr Pro Lys Glu Pro Ala Pro
    50                  55                  60

Thr Thr Pro Lys Glu Pro Ala Pro Thr Thr Thr Lys Glu Pro Ala Pro
65              70                  75                  80

Thr Thr Thr Lys Ser Ala Pro Thr Thr Pro Lys Glu Pro Ala Pro Thr
                85                  90                  95

Thr Pro Lys Glu Pro Ala Pro Thr Thr Thr Lys Glu Pro Ala Pro Thr
            100                 105                 110

Thr Thr Lys Ser Ala Pro Thr Thr Pro Lys Glu Pro Ala Pro Thr Thr
        115                 120                 125

Pro Lys Glu Pro Lys Pro Ala Pro Thr Thr Pro
    130                 135

<210> SEQ ID NO 22
<211> LENGTH: 3303
<212> TYPE: DNA
<213> ORGANISM: Artificial Sequence
<220> FEATURE:
<223> OTHER INFORMATION: Recombinant PRG4-Lub:5 cDNA construct

<400> SEQUENCE: 22
atggcatgga aaacacttcc catttacctg ttgttgctgc tgtctgtttt cgtgattcag        60
caagtttcat ctcaagattt atcaagctgt gcagggagat gtggggaagg gtattctaga       120
gatgccacct gcaactgtga ttataactgt caacactaca tggagtgctg ccctgatttc       180
aagagagtct gcactgcgga gctttcctgt aaaggccgct gctttgagtc cttcgagaga       240
gggagggagt gtgactgcga cgcccaatgt aagaagtatg acaagtgctg tcccgattat       300
gagagttttc gtgcagaagt gcataatccc acatcaccac catcttcaaa gaaagcacct       360
ccaccttcag gagcatctca aaccatcaaa tcaacaacca aacgttcacc caaaccacca       420
aacaagaaga gactaagaa agttatagaa tcagaggaaa taacagaaga acattctgtt       480
tctgaaaatc aagagtcctc ctccagtagc agttcaagta gttcgtcgtc gacaatttgg       540
aaaatcaagt cttccaaaaa ttcagctgct aatagagaat acagaagaa actcaaagta       600 aaagataaca agaagaacag aactaaaaag aaacctaccc ccaaaccacc agttgtagat       660
gaagctggaa gtggattgga caatggtgac ttcaaggtca caactcctga cacgtctacc       720
acccaacaca taaagtcag cacatctccc aagatcacaa cagcaaaacc aataaatccc       780
agacccagtc ttccacctaa ttctgataca tctaaagaga cgtctttgac agtgaataaa       840
gagacaacag ttgaaactaa agaaactact acaacaaata acagacttc aactgatgga       900 aaagagaaga ctacttccgc taaagagaca caaagtatag agaaacatc tgctaaagat       960 ttagcaccca catctaaagt gctggctaaa cctacaccca agctgaaac tacaaccaaa      1020 ggccctgctc tcaccactcc caaggagccc acgccacca ctcccaagga gcctgcatct      1080
accacaccca agagcccac acctaccacc atcaagagcg cgcccacaac tccaaaagag      1140
```

```
cccgcaccta ccacgacaaa gtcagctcct actacgccca aagagccagc gccgacgact    1200
actaaagaac cggcacccac cacgcctaaa gaaccagccc ctactacgac aaaggagcct    1260
gcacccacaa ccacgaagag cgcacccaca acaccaaagg agccggcccc tacgactcct    1320
aaagaaccag cccctactac gacaaaggag cctgcaccca caaccacgaa gagcgcaccc    1380
acaacaccaa aggagccggc ccctacgact cctaaagaac cagccccctac tacgacaaag    1440 gagcctgcac ccacaaccac gaagagcgca cccacaacac caaggagcc ggcccctacg    1500 actcctaaag aaccagcccc tactacgaca aaggagcctg cacccacaac cacgaagagc    1560
gcacccacaa caccaaagga gccggccccct acgactccta aggaacccaa accggcacca    1620
accactccgg aaacacctcc tccaaccact tcagaggtct ctactccaac taccaccaag    1680
gagcctacca ctatccacaa agccctgat gaatcaactc ctgagctttc tgcagaaccc    1740
acaccaaaag ctcttgaaaa cagtcccaag gaacctggtg tacctacaac taagacgccg    1800
gcggcgacta aacctgaaat gactacaaca gctaaagaca agacaacaga aagagactta    1860
cgtactacac ctgaaactac aactgctgca cctaagatga caaaagagac agcaactaca    1920
acagaaaaaa ctaccgaatc caaaataaca gctacaacca cacaagtaac atctaccaca    1980
actcaagata ccacaccatt caaaattact actcttaaaa caactactct tgcacccaaa    2040
gtaactacaa caaaaaagac aattactacc actgagatta tgaacaaacc tgaagaaaca    2100
gctaaaccaa aagacagagc tactaattct aaagcgacaa ctcctaaacc tcaaaagcca    2160
accaaagcac ccaaaaaacc cacttctacc aaaaagccaa aaacaatgcc tagagtgaga    2220
aaaccaaaga cgacaccaac tccccgcaag atgacatcaa caatgccaga attgaaccct    2280
acctcaagaa tagcagaagc catgctccaa accaccacca gacctaacca aactccaaac    2340
tccaaactag ttgaagtaaa tccaaagagt gaagatgcag gtggtgctga aggagaaaca    2400
cctcatatgc ttctcaggcc ccatgtgttc atgcctgaag ttactcccga catggattac    2460
ttaccgagag tacccaatca aggcattatc atcaatccca tgctttccga tgagaccaat    2520
atatgcaatg gtaagccagt agatggactg actactttgc gcaatgggac attagttgca    2580
ttccgaggtc attatttctg gatgctaagt ccattcagtc caccatctcc agctcgcaga    2640
attactgaag tttgggggtat tccttccccc attgatactg ttttttactag gtgcaactgt    2700 gaaggaaaaa ctttcttctt taaggattct cagtactggc gttttaccaa tgatataaaa    2760
gatgcagggt accccaaacc aatttttcaaa ggatttggag gactaactgg acaaatagtg    2820
gcagcgcttt caacagctaa atataagaac tggcctgaat ctgtgtattt tttcaagaga    2880
ggtggcagca ttcagcagta tatttataaa caggaacctg tacagaagtg ccctggaaga    2940
aggcctgctc taaattatcc agtgtatgga gaaatgacac aggttaggag acgtcgcttt    3000
gaacgtgcta taggaccttc tcaaacacac accatcagaa ttcaatattc acctgccaga    3060
ctggcttatc aagacaaagg tgtccttcat aatgaagtta agtgagtat actgtggaga    3120 ggacttccaa atgtggttac ctcagctata tcactgccca acatcagaaa acctgacggc    3180
tatgattact atgcctttttc taaagatcaa tactataaca ttgatgtgcc tagtagaaca    3240
gcaagagcaa ttactactcg ttctgggcag accttatcca aagtctggta caactgtcct    3300
taa                                                                  3303

<210> SEQ ID NO 23
<211> LENGTH: 1100
<212> TYPE: PRT
```

<213> ORGANISM: Artificial Sequence
<220> FEATURE:
<223> OTHER INFORMATION: Amino acid sequence of entire PRG4-LUB:5 protein.

<400> SEQUENCE: 23

```
Met Ala Trp Lys Thr Leu Pro Ile Tyr Leu Leu Leu Leu Leu Ser Val
1               5                   10                  15

Phe Val Ile Gln Gln Val Ser Ser Gln Asp Leu Ser Ser Cys Ala Gly
            20                  25                  30

Arg Cys Gly Glu Gly Tyr Ser Arg Asp Ala Thr Cys Asn Cys Asp Tyr
        35                  40                  45

Asn Cys Gln His Tyr Met Glu Cys Cys Pro Asp Phe Lys Arg Val Cys
    50                  55                  60

Thr Ala Glu Leu Ser Cys Lys Gly Arg Cys Phe Glu Ser Phe Glu Arg
65                  70                  75                  80

Gly Arg Glu Cys Asp Cys Asp Ala Gln Cys Lys Lys Tyr Asp Lys Cys
                85                  90                  95

Cys Pro Asp Tyr Glu Ser Phe Cys Ala Glu Val His Asn Pro Thr Ser
            100                 105                 110

Pro Pro Ser Ser Lys Lys Ala Pro Pro Ser Gly Ala Ser Gln Thr
        115                 120                 125

Ile Lys Ser Thr Thr Lys Arg Ser Pro Lys Pro Asn Lys Lys
    130                 135                 140

Thr Lys Lys Val Ile Glu Ser Glu Glu Ile Thr Glu Glu His Ser Val
145                 150                 155                 160

Ser Glu Asn Gln Glu Ser Ser Ser Ser Ser Ser Ser Ser Ser Ser Ser
                165                 170                 175

Ser Thr Ile Trp Lys Ile Lys Ser Ser Lys Asn Ser Ala Ala Asn Arg
            180                 185                 190

Glu Leu Gln Lys Lys Leu Lys Val Lys Asp Asn Lys Lys Asn Arg Thr
        195                 200                 205

Lys Lys Lys Pro Thr Pro Lys Pro Pro Val Val Asp Glu Ala Gly Ser
    210                 215                 220

Gly Leu Asp Asn Gly Asp Phe Lys Val Thr Thr Pro Asp Thr Ser Thr
225                 230                 235                 240

Thr Gln His Asn Lys Val Ser Thr Ser Pro Lys Ile Thr Thr Ala Lys
                245                 250                 255

Pro Ile Asn Pro Arg Pro Ser Leu Pro Pro Asn Ser Asp Thr Ser Lys
            260                 265                 270

Glu Thr Ser Leu Thr Val Asn Lys Glu Thr Thr Val Glu Thr Lys Glu
        275                 280                 285

Thr Thr Thr Thr Asn Lys Gln Thr Ser Thr Asp Gly Lys Glu Lys Thr
    290                 295                 300

Thr Ser Ala Lys Glu Thr Gln Ser Ile Glu Lys Thr Ser Ala Lys Asp
305                 310                 315                 320

Leu Ala Pro Thr Ser Lys Val Leu Ala Lys Pro Thr Pro Lys Ala Glu
                325                 330                 335

Thr Thr Thr Lys Gly Pro Ala Leu Thr Thr Pro Lys Glu Pro Thr Pro
            340                 345                 350

Thr Thr Pro Lys Glu Pro Ala Ser Thr Thr Pro Lys Glu Pro Thr Pro
        355                 360                 365

Thr Thr Ile Lys Ser Ala Pro Thr Thr Pro Lys Glu Pro Ala Pro Thr
    370                 375                 380
```

```
Thr Thr Lys Ser Ala Pro Thr Thr Pro Lys Glu Pro Ala Pro Thr Thr
385                 390                 395                 400

Thr Lys Glu Pro Ala Pro Thr Thr Pro Lys Glu Pro Ala Pro Thr Thr
                405                 410                 415

Thr Lys Glu Pro Ala Pro Thr Thr Lys Ser Ala Pro Thr Thr Pro
        420                 425                 430

Lys Glu Pro Ala Pro Thr Thr Pro Lys Glu Pro Ala Pro Thr Thr Thr
    435                 440                 445

Lys Glu Pro Ala Pro Thr Thr Lys Ser Ala Pro Thr Thr Pro Lys
    450                 455                 460

Glu Pro Ala Pro Thr Thr Pro Lys Glu Pro Ala Pro Thr Thr Thr Lys
465                 470                 475                 480

Glu Pro Ala Pro Thr Thr Lys Ser Ala Pro Thr Thr Pro Lys Glu
                485                 490                 495

Pro Ala Pro Thr Thr Pro Lys Glu Pro Ala Pro Thr Thr Thr Lys Glu
            500                 505                 510

Pro Ala Pro Thr Thr Thr Lys Ser Ala Pro Thr Thr Pro Lys Glu Pro
            515                 520                 525

Ala Pro Thr Thr Pro Lys Glu Pro Lys Pro Ala Pro Thr Thr Pro Glu
    530                 535                 540

Thr Pro Pro Pro Thr Thr Ser Glu Val Ser Thr Pro Thr Thr Thr Lys
545                 550                 555                 560

Glu Pro Thr Thr Ile His Lys Ser Pro Asp Glu Ser Thr Pro Glu Leu
            565                 570                 575

Ser Ala Glu Pro Thr Pro Lys Ala Leu Glu Asn Ser Pro Lys Glu Pro
            580                 585                 590

Gly Val Pro Thr Thr Lys Thr Pro Ala Ala Thr Lys Pro Glu Met Thr
            595                 600                 605

Thr Thr Ala Lys Asp Lys Thr Thr Glu Arg Asp Leu Arg Thr Thr Pro
    610                 615                 620

Glu Thr Thr Thr Ala Ala Pro Lys Met Thr Lys Glu Thr Ala Thr Thr
625                 630                 635                 640

Thr Glu Lys Thr Thr Glu Ser Lys Ile Thr Ala Thr Thr Thr Gln Val
                645                 650                 655

Thr Ser Thr Thr Thr Gln Asp Thr Thr Pro Phe Lys Ile Thr Thr Leu
            660                 665                 670

Lys Thr Thr Thr Leu Ala Pro Lys Val Thr Thr Thr Lys Lys Thr Ile
            675                 680                 685

Thr Thr Thr Glu Ile Met Asn Lys Pro Glu Glu Thr Ala Lys Pro Lys
    690                 695                 700

Asp Arg Ala Thr Asn Ser Lys Ala Thr Thr Pro Lys Pro Gln Lys Pro
705                 710                 715                 720

Thr Lys Ala Pro Lys Lys Pro Thr Ser Thr Lys Lys Pro Lys Thr Met
                725                 730                 735

Pro Arg Val Arg Lys Pro Lys Thr Thr Pro Thr Pro Arg Lys Met Thr
            740                 745                 750

Ser Thr Met Pro Glu Leu Asn Pro Thr Ser Arg Ile Ala Glu Ala Met
            755                 760                 765

Leu Gln Thr Thr Thr Arg Pro Asn Gln Thr Pro Asn Ser Lys Leu Val
    770                 775                 780

Glu Val Asn Pro Lys Ser Glu Asp Ala Gly Gly Ala Glu Gly Glu Thr
785                 790                 795                 800

Pro His Met Leu Leu Arg Pro His Val Phe Met Pro Glu Val Thr Pro
```

```
                  805                 810                 815
Asp Met Asp Tyr Leu Pro Arg Val Pro Asn Gln Gly Ile Ile Ile Asn
        820                 825                 830

Pro Met Leu Ser Asp Glu Thr Asn Ile Cys Asn Gly Lys Pro Val Asp
        835                 840                 845

Gly Leu Thr Thr Leu Arg Asn Gly Thr Leu Val Ala Phe Arg Gly His
        850                 855                 860

Tyr Phe Trp Met Leu Ser Pro Phe Ser Pro Ser Pro Ala Arg Arg
865                 870                 875                 880

Ile Thr Glu Val Trp Gly Ile Pro Ser Pro Ile Asp Thr Val Phe Thr
                    885                 890                 895

Arg Cys Asn Cys Glu Gly Lys Thr Phe Phe Phe Lys Asp Ser Gln Tyr
        900                 905                 910

Trp Arg Phe Thr Asn Asp Ile Lys Asp Ala Gly Tyr Pro Lys Pro Ile
        915                 920                 925

Phe Lys Gly Phe Gly Gly Leu Thr Gly Gln Ile Val Ala Ala Leu Ser
        930                 935                 940

Thr Ala Lys Tyr Lys Asn Trp Pro Glu Ser Val Tyr Phe Phe Lys Arg
945                 950                 955                 960

Gly Gly Ser Ile Gln Gln Tyr Ile Tyr Lys Gln Glu Pro Val Gln Lys
                965                 970                 975

Cys Pro Gly Arg Arg Pro Ala Leu Asn Tyr Pro Val Tyr Gly Glu Met
                980                 985                 990

Thr Gln Val Arg Arg Arg Phe  Glu Arg Ala Ile Gly  Pro Ser Gln
            995                 1000                1005

Thr His  Thr Ile Arg Ile Gln  Tyr Ser Pro Ala Arg  Leu Ala Tyr
    1010                1015                1020

Gln Asp  Lys Gly Val Leu His  Asn Glu Val Lys Val  Ser Ile Leu
    1025                1030                1035

Trp Arg  Gly Leu Pro Asn Val  Val Thr Ser Ala Ile  Ser Leu Pro
    1040                1045                1050

Asn Ile  Arg Lys Pro Asp Gly  Tyr Asp Tyr Tyr Ala  Phe Ser Lys
    1055                1060                1065

Asp Gln  Tyr Tyr Asn Ile Asp  Val Pro Ser Arg Thr  Ala Arg Ala
    1070                1075                1080

Ile Thr  Thr Arg Ser Gly Gln  Thr Leu Ser Lys Val  Trp Tyr Asn
    1085                1090                1095

Cys Pro
    1100

<210> SEQ ID NO 24
<211> LENGTH: 514
<212> TYPE: DNA
<213> ORGANISM: Artificial Sequence
<220> FEATURE:
<223> OTHER INFORMATION: Lub:5 DNA insert from cDNA cassette-1 and four
      synthetic cDNA cassette-2 sequences

<400> SEQUENCE: 24
gcgcgcccac aactccaaaa gagcccgcac ctaccacgac aaagtcagct cctactacgc      60
ccaaagagcc agcgccgacg actactaaag aaccggcacc caccacgcct aaagaaccag    120 ccctactac gacaaaggag cctgcaccca aaccacgaa gagcgcaccc acaacaccaa      180
aggagccggc ccctacgact cctaaagaac cagcccctac tacgacaaag gagcctgcac    240
ccacaaccac gaagagcgca cccacaacac caaaggagcc ggcccctacg actcctaaag    300
```

```
aaccagcccc tactacgaca aaggagcctg cacccacaac cacgaagagc gcacccacaa      360
caccaaagga gccggcccct acgactccta agaaccagc ccctactacg acaaaggagc      420
ctgcacccac aaccacgaag agcgcacccca caacaccaaa ggagccggcc cctacgactc    480
ctaaggaacc caaaccggca ccaaccactc cgga                                  514
```

<210> SEQ ID NO 25
<211> LENGTH: 170
<212> TYPE: PRT
<213> ORGANISM: Artificial Sequence
<220> FEATURE:
<223> OTHER INFORMATION: 170 amino acids encoded by Lub:5 DNA insert (15
      KEPAPTT sequences between S373 and E544 in SEQ ID NO: 23)

<400> SEQUENCE: 25

```
Ala Pro Thr Thr Pro Lys Glu Pro Ala Pro Thr Thr Lys Ser Ala
1               5                   10                  15

Pro Thr Thr Pro Lys Glu Pro Ala Pro Thr Thr Lys Glu Pro Ala
            20                  25                  30

Pro Thr Thr Pro Lys Glu Pro Ala Pro Thr Thr Lys Glu Pro Ala
        35                  40                  45

Pro Thr Thr Thr Lys Ser Ala Pro Thr Thr Pro Lys Glu Pro Ala Pro
    50                  55                  60

Thr Thr Pro Lys Glu Pro Ala Pro Thr Thr Lys Glu Pro Ala Pro
65                  70                  75                  80

Thr Thr Thr Lys Ser Ala Pro Thr Thr Pro Lys Glu Pro Ala Pro Thr
                85                  90                  95

Thr Pro Lys Glu Pro Ala Pro Thr Thr Lys Glu Pro Ala Pro Thr
            100                 105                 110

Thr Thr Lys Ser Ala Pro Thr Thr Pro Lys Glu Pro Ala Pro Thr Thr
            115                 120                 125

Pro Lys Glu Pro Ala Pro Thr Thr Lys Glu Pro Ala Pro Thr Thr
        130                 135                 140

Thr Lys Ser Ala Pro Thr Thr Pro Lys Glu Pro Ala Pro Thr Thr Pro
145                 150                 155                 160

Lys Glu Pro Lys Pro Ala Pro Thr Thr Pro
                165                 170
```

<210> SEQ ID NO 26
<211> LENGTH: 45
<212> TYPE: PRT
<213> ORGANISM: Artificial Sequence
<220> FEATURE:
<223> OTHER INFORMATION: amino acid sequence
      "APTTPKEPAPTTTKSAPTTPKEPAPTTTKEPAPTTPKEPAPTTTK" (45 amino acids)
      in preferred PRG4-LUB:N protein

<400> SEQUENCE: 26

```
Ala Pro Thr Thr Pro Lys Glu Pro Ala Pro Thr Thr Lys Ser Ala
1               5                   10                  15

Pro Thr Thr Pro Lys Glu Pro Ala Pro Thr Thr Lys Glu Pro Ala
            20                  25                  30

Pro Thr Thr Pro Lys Glu Pro Ala Pro Thr Thr Lys
        35                  40                  45
```

<210> SEQ ID NO 27
<211> LENGTH: 31
<212> TYPE: PRT
<213> ORGANISM: Artificial Sequence -continued

```
<220> FEATURE:
<223> OTHER INFORMATION: amino acid sequence
      "KEPAPTTTKEPAPTTTKSAPTTPKEPAPTTP" (31 amino acids) repeated N-1
      times in preferred PRG4-LUB:N protein

<400> SEQUENCE: 27

Lys Glu Pro Ala Pro Thr Thr Thr Lys Glu Pro Ala Pro Thr Thr Thr
1               5                   10                  15

Lys Ser Ala Pro Thr Thr Pro Lys Glu Pro Ala Pro Thr Thr Pro
            20                  25                  30

<210> SEQ ID NO 28
<211> LENGTH: 22
<212> TYPE: PRT
<213> ORGANISM: Artificial Sequence
<220> FEATURE:
<223> OTHER INFORMATION: Amino acid sequence "EPAPTTTKSAPTTPKEPAPTTP"
      (22 amino acids) joining SEQ ID NO: 26 to (N-2) repeats of SEQ ID
      NO: 27 in preferred PRG4-LUB:N protein where N = 3 or more.

<400> SEQUENCE: 28

Glu Pro Ala Pro Thr Thr Thr Lys Ser Ala Pro Thr Thr Pro Lys Glu
1               5                   10                  15

Pro Ala Pro Thr Thr Pro
            20

<210> SEQ ID NO 29
<211> LENGTH: 10
<212> TYPE: PRT
<213> ORGANISM: Artificial Sequence
<220> FEATURE:
<223> OTHER INFORMATION: Amino acid sequence "KEPKPAPTTP" (10 amino
      acids) in preferred PRG4-LUB:N protein where N = 2 or more.

<400> SEQUENCE: 29

Lys Glu Pro Lys Pro Ala Pro Thr Thr Pro
1               5                   10
```

RECOMBINANT LUBRICIN MOLECULES AND USES THEREOF

This application is a divisional of U.S. application Ser. No. 10/567,764, filed Sep. 27, 2006, now U.S. Pat. No. 7,642,236, which claims priority from International Application No. PCT/US2004/026508, filed Aug. 13, 2004, which in turn claims priority from U.S. Provisional Application No. 60/495,741, filed Aug. 14, 2003. The disclosure of the prior applications are incorporated by reference in their entirety in this application.

The invention relates to novel recombinant lubricin molecules and their uses as lubricants, anti-adhesive agents and/or intra-articular supplements for, e.g., synovial joints, meniscus, tendon, peritoneum, pericardium and pleura.

BACKGROUND OF THE INVENTION

Optimal functionality of synovial joints is dependent upon extremely low coefficients of friction between articulating tissues. Normally, a contiguous, well-lubricated surface is maintained on articular cartilage. During osteoarthritis (OA), however, reduced lubrication contributes to cartilage matrix degradation, and fibrillation; these in turn contribute to joint dysfunction and pain. Reduced lubrication also leads to joint dysfunction and pain in other forms of arthritis, including rheumatoid arthritis (RA).

For other tissues (e.g., tendons), a lubricated surface also contributes to optimal functionality. In addition to requiring a lubricated surface, normal tendon function requires the prevention of cellular adhesion to tendon surfaces. In flexor tendon injury and repair, for example, the formation of tendon adhesions is the most common complication.

Native lubricin protein is related to megakaryocyte stimulating factor (MSF) precursor protein. PRG4 (proteoglycan 4) is the name for MSF that has been accepted for the UCL/HGNC/HUGO Human Gene Nomenclature database. PRG4 protein (i.e., the MSF precursor protein) is described in U.S. Pat. No. 6,433,142 and US20020137894 (all patents and patent applications cited in this document are incorporated by reference in their entirety). Polypeptide encoded by exon 6 of the PRG4 gene is heavily glycosylated and appears necessary for a PRG4-related protein to serve as a lubricant, e.g., between surfaces of articular cartilage.

Studies indicate that PRG4 glycoprotein is also synthesized by the intimal synoviocytes that line tendon sheaths; it is highly likely that the glycoprotein also originates from tenocytes (Rees et al., 2002). The glycoprotein is prominently present in fibrocartilaginous regions of tendon. In a manner complementary to its synovial-fluid function, the glycoprotein may play an important cytoprotective role for tendons by preventing cellular adhesion to tendon surfaces, as well as by providing lubrication during normal tendon function.

Exon 6 of the PRG4 (also called "lubricin") gene encodes approximately 76-78 repeats of KEPAPTT-similar sequences and 6 repeats of XXTTTX-like sequences. Varying the number of comparable repeat sequences in recombinant lubricin proteins according to the present invention allows for development of improved biotherapeutics for enhancing lubrication in joints and for countering undesired adhesion between tissues.

SUMMARY OF THE INVENTION

The present invention relates to novel recombinant lubricin molecules and their use as lubricants, anti-adhesive agents and/or intra-articular supplements.

In order to optimize expression parameters and investigate the functional necessity of all approximately 76-78 KEPAPTT-similar sequences, lubricin expression constructs were designed which enabled the synthesis of recombinant lubricin proteins with varying degrees of O-linked oligosaccharide substitution. This is accomplished by incorporating variable numbers of the KEPAPTT-like sequences into a "core" cDNA construct comprised of exons 1 through 5,5'- and 3'-flanking regions of exon 6, and exons 7 through 12. Iterative insertion of "synthetic cDNA cassettes" encoding multiple KEPAPTT-like sequences facilitates the generation of recombinant lubricin constructs of different sizes. The initial focus of these studies was on construct PRG4-Lub:1 (containing DNA of "synthetic cDNA cassette-1" (SEQ ID NO: 1), which encodes four KEPAPTT sequences).

The recombinant lubricin proteins of the present invention share primary structure with several isoforms of native human lubricin (see U.S. Pat. No. 6,743,774, US20040072741, and WO0064930). Among characterized isoforms, each isoform differs in the composition of PRG4 gene exons that encode the isoform's primary structure. For example, exons 1 through 12 of the PRG4 gene encode the V0 isoform, which represents the full-length isoform, while exons 1 through 4 and 6 through 12 encode the V1 isoform, which lacks only a segment encoded by exon 5. Exons 1 through 3 and 6 through 12 encode the V2 isoform, which lacks segments encoded by exons 4 and 5. Finally, exons 1, 3, and 6 through 12 encode the V3 isoform, which lacks segments encoded by exons 2, 4, and 5. Other isoforms likely exist, and some related mutant proteins have been described (see US20020086824).

In particular, the present invention provides recombinant lubricin protein comprising repetitive KEPAPTT-like sequences. In preferred embodiments, the invention provides isolated protein comprising SEQ ID NOS: 9, 13, 17, 21 or 25. The invention provides in related embodiments isolated protein comprising SEQ ID NOS: 7, 11, 15, 19 or 23. In further related embodiments, the invention provides isolated polynucleotide comprising nucleic acid sequence encoding recombinant lubricin protein. In preferred embodiments, the invention provides isolated polynucleotide comprising nucleic acid sequence encoding the protein. In further related embodiments, the invention provides isolated polynucleotide having at least 80%, 85%, 90%, 95%, 97%, 98% or 99% identity to SEQ ID NOS: 6, 10, 14, 18 or 22 over the entire length of the sequence.

In related aspects, the present invention also provides an isolated protein comprising SEQ ID NO: 26 joined to (N minus 2) repeat(s) of SEQ ID NO: 27, where N equals an integer from 3 through 200. In further related embodiments, the present invention provides an isolated protein comprising SEQ ID NO: 26 plus SEQ ID NO: 28 plus [(N minus 2) repeat(s) of SEQ ID NO: 27] plus SEQ ID NO: 29, where N equals an integer from 3 through 200. In embodiments of the related aspects of the invention noted in this paragraph, more preferably N equals an integer from 5 through 50, and even more preferably N equals an integer from 10 through 30.

TABLE 1

Identification of Sequences Having Sequence Identifiers

| SEQ ID NO: | Identification |
|---|---|
| 1 | nucleotide sequence of synthetic cDNA cassette-1: 155 bases |
| 2 | translation of SEQ ID NO: 1: 51 amino acids |
| 3 | nucleotide sequence of synthetic cDNA cassette-2: 125 bases |
| 4 | translation of SEQ ID NO: 3: 41 amino acids |
| 5 | pTmed2 vector containing recombinant PRG4-Lub:1 cDNA construct: 8049 bases |
| 6 | recombinant PRG4-Lub:1 cDNA construct: 2946 bases |
| 7 | amino acid sequence of entire PRG4-LUB:1 protein: 981 amino acids |
| 8 | Lub:1 DNA insert from synthetic cDNA cassette-1: 157 bases |
| 9 | 51 amino acids encoded by Lub:1 DNA insert (4 KEPAPTT sequences between S373 to E425 in SEQ ID NO: 7) |
| 10 | recombinant PRG4-Lub:2 cDNA construct: 3024 bases |
| 11 | amino acid sequence of entire PRG4-LUB:2 protein: 1007 amino acids |
| 12 | Lub:2 DNA insert from synthetic cDNA cassette-1 and one synthetic cDNA cassette-2 sequence: 235 bases |
| 13 | 77 amino acids encoded by Lub:2 DNA insert (6 KEPAPTT sequences between S373 and E451 in SEQ ID NO: 11) |
| 14 | recombinant PRG4-Lub:3 cDNA construct: 3117 bases |
| 15 | amino acid sequence of entire PRG4-LUB:3 protein: 1038 ammo acids |
| 16 | Lub:3 DNA insert from synthetic cDNA cassette-1 and two synthetic cDNA cassette-2 sequences: 328 bases |
| 17 | 108 amino acids encoded by Lub:3 DNA insert (9 KEPAPTT sequences between S373 and E482 in SEQ ID NO: 15) |
| 18 | recombinant PRG4-Lub:4 cDNA construct: 3210 bases |
| 19 | amino acid sequence of entire PRG4-LUB:4 protein: 1069 amino acids |
| 20 | Lub:4 DNA insert from cDNA cassette-1 and three synthetic cDNA cassette-2 sequences: 421 bases |
| 21 | 139 amino acids encoded by Lub:4 DNA insert (12 KEPAPTT sequences between S373 and E513 in SEQ ID NO: 19) |
| 22 | recombinant PRG4-Lub:5 cDNA construct: 3303 bases |
| 23 | amino acid sequence of entire PRG4-LUB:5 protein: 1100 amino acids |
| 24 | Lub:5 DNA insert from cDNA cassette-1 and four synthetic cDNA cassette-2 sequences: 514 bases |
| 25 | 170 amino acids encoded by Lub:5 DNA insert (15 KEPAPTT sequences between S373 and E544 in SEQ ID NO: 23) |
| 26 | amino acid sequence "APTTPKEPAPTTTKSAPTTPKEPAPTTT KEPAPTTPKEPAPTTTK" (45 amino acids) in preferred PRG4-LUB:N protein |
| 27 | amino acid sequence "KEPAPTTTKEPAPTTTKSAPTTP KEPAPTTP" (31 amino acids) repeated N-1 times in preferred PRG4-LUB:N protein |
| 28 | amino acid sequence "EPAPTTTKSAPTTPKEPAPTTP" (22 amino acids) joining SEQ ID NO: 26 to (N-2) repeats of SEQ ID NO: 27 in preferred PRG4-LUB:N protein where N ≧ 3. |
| 29 | amino acid sequence "KEPKPAPTTP" (10 amino acids) in preferred PRG4-LUB:N protein where N ≧ 2. |

The invention also provides in related embodiments a composition comprising a therapeutically effective amount of a recombinant lubricin protein in a pharmaceutically acceptable carrier. In some embodiments, the composition additionally comprises hyaluronan or hylan.

The invention further provides a method of treating a subject comprising: obtaining a recombinant lubricin protein composition; and administering said composition to a tissue of the subject. In related embodiments of this method of the invention, the tissue is selected from the group consisting of cartilage, synovium, meniscus, tendon, peritoneum, pericardium, and pleura. In further related embodiments of this method of the invention, the method additionally comprises a step selected from the group consisting of providing an anesthetic to the subject; providing an anti-inflammatory drug to the subject; providing an antibiotic to the subject; aspirating fluid from the subject; washing tissue of the subject; and imaging tissue of the subject. In other related embodiments, the subject is selected from the group consisting of a mouse, a rat, a cat, a dog, a horse, and a human.

In other embodiments, the invention also provides an expression vector comprising a polynucleotide encoding a recombinant lubricin protein wherein the polynucleotide is operably linked to an expression control sequence. In related embodiments, the invention provides a method of producing recombinant lubricin protein comprising: growing cells transformed with the expression vector in liquid culture media; and collecting recombinant lubricin protein from the media. The collecting protein step may further comprise: concentrating the protein by filtering the media through a membrane; collecting the retained protein from the membrane; and solubilizing the collected protein in a buffered salt solution containing L-arginine hydrochloride ranging in concentration from 0.1 to 2.0 M.

In another related embodiment, the invention provides isolated antibody specific for a recombinant lubricin protein.

Other features and advantages of the invention will be apparent from the following description of preferred embodiments thereof, and from the claims.

DETAILED DESCRIPTION OF THE INVENTION

The base DNA construct utilized in generating recombinant lubricin proteins may include variable arrangements of sequences 5' and 3' of exon 6 of the PRG4 gene. For example, the base DNA construct may include variable arrangements of sequences encoding somatomedin B-like domains (exons 2 through 4) or hemopexin-like domains (exons 7 through 9).

Embodiments of the base DNA construct having various exon arrangements 3' of exon 6 may include base DNA constructs that include only exon 7, 8, 9, 10, 11, or 12 individually, or exon pairs (7 and 8), (7 and 9), (7 and 10), (7 and 11), (7 and 12), (8 and 9), (8 and 10), (8 and 11), (8 and 12), (9 and 10), (9 and 11), (9 and 12), (10 and 11), (10 and 12), or (11 and 12), or exon triplets (7, 8 and 9), (7, 8 and 10), (7, 8, and 11), (7, 8, and 12), (7, 9 and 10), (7, 9 and 11), (7, 9 and 12), (7, 10 and 11), (7, 10 and 12), (7, 11 and 12), (8, 9 and 10), (8, 9 and 11), (8, 9 and 12), (8, 10 and 11), (8, 10 and 12), (8, 11 and 12), (9, 10 and 11), (9, 10 and 12), (9, 11 and 12), or (10, 11 and 12), or exon quadruplets (7, 8, 9 and 10), (7, 8, 9 and 11), (7, 8, 9 and 12), (7, 8, 10 and 11), (7, 8, and 12), (7, 8, 11 and 12), (7, 9, 10 and 11), (7, 9, 10 and 12), (7, 9, 11 and 12), (7, 10, 11 and 12), (8, 9, 10 and 11), (8, 9, 10 and 12), (8, 9, 11 and 12), (8, 10, 11 and 12), or (9, 10, 11 and 12), or exon quintets (7, 8, 9, 10 and 11), (7, 8, 9, 10 and 12), (7, 8, 9, 11 and 12), (7, 8, 10, 11 and 12), (7, 9, 10, 11 and 12), or (8, 9, 10, 11 and 12), or exon sextet (7, 8, 9, 10, 11 and 12).

In addition, embodiments of the base DNA construct having various exon arrangements 5' of exon 6 may include base DNA constructs that include only exon 1, 2, 3, 4, or 5 individually, or exon pairs (1 and 2), (1 and 3), (1 and 4), (1 and 5), (2 and 3), (2 and 4), (2 and 5), (3 and 4), (3 and 5), or (4 and 5), or exon triplets (1, 2 and 3), (1, 2 and 4), (1, 2 and 5), (1, 3 and 4), (1, 3 and 5), (1, 4 and 5), (2, 3 and 4), (2, 3 and 5), (2, 4 and 5), or (3, 4 and 5), or exon quadruplets (1, 2, 3 and 4), (1, 2, 3 and 5), (1, 2, 4 and 5), (1, 3, 4 and 5), or (2, 3, 4 and 5), or exon quintets (1, 2, 3, 4 and 5).

The present invention also encompasses proteins encoded by base DNA constructs, i.e., wherein part or all of exon 6 sequence-encoded polypeptide is deleted and no amino acids encoded by inserts from synthetic cDNA cassettes have been added.

The present invention also encompasses polynucleotides that are homologous to the specific embodiments outlined herein, e.g., having at least 80%, 85%, 90%, 95%, 97%, 98% or 99% sequence identity to the specified DNA sequences. The invention further includes polynucleotides having nucleic acid sequence capable of hybridizing over the length of a functional domain to the complement of the specified DNA sequences under high stringency conditions. The invention also includes proteins encoded by these homologous or hybridizing polynucleotides.

In order to delineate more clearly embodiments of the present invention, the following definitions are provided.

Definitions. The phrase "repetitive KEPAPTT-like sequence" means an amino acid sequence having at least 90%, 93%, 95%, 96%, 97%, 98%, 99% or higher identity to: (a) sequence "APTTPKEPAPTTTKSAPTTPKEPAPTTT-KEPAPTTPKEPAPTTTK" (SEQ ID NO: 26; 45 amino acids) and having at least one O-linked substitution; (b) sequence "KEPAPTTTKEPAPTTTKSAPTTPKEPAPTTP" (SEQ ID NO: 27; 31 amino acids) and having at least one O-linked substitution; or (c) sequence "EPAPTTTKSAPT-TPKEPAPTTP" (SEQ ID NO: 28; 22 amino acids) and having at least one O-linked substitution. A repetitive KEPAPTT-like sequence may preferably have two, three, four or more O-linked substitutions.

While there exist a number of methods to measure identity between two polynucleotide or polypeptide sequences, the term "identity" is well known to skilled artisans and has a definite meaning with respect to a given specified method. Sequence identity described herein is measured using the BLAST 2 SEQUENCES tool available through NCBI (http://www.ncbi.nlm.nih.gov/blast/; see also Tatusova and Madden (1999)). For amino acid sequences, the parameters used are expect=1000; word size=2; filter=off; and other parameters set to default values. These same parameters are used for nucleic acid sequences, except word size=8. Default values for amino acid sequence comparisons are: Matrix=BLOSUM62; open gap=11; extension gap=1 penalties; and gap x_dropoff=50. Default values for nucleic acid sequence comparisons are: reward for a match=1; penalty for a mismatch=−2; strand option=both strands; open gap=5; extension gap=2 penalties; and gap x_dropoff=50.

An O-linked substitution of recombinant lubricin may be a substitution with the lubricating oligosaccharide β-(1-3)-Gal-GalNac, or with other moieties, including artificial or naturally-occurring carbohydrate moieties (such as keratan sulfate or chondroitin sulfate). In some embodiments, the O-linked substitution may be with moieties that contribute to a capacity of recombinant lubricin to act as a carrier of surface active phospholipid (SAPL) or surfactants (Hills, 2002). Percent glycosylation or substitution is determined by weight (dry weight).

High stringency conditions, when used in reference to DNA:DNA hybridization, comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42° C. when a probe of about 500 nucleotides in length is employed.

Polypeptides or other compounds described herein are said to be "isolated" when they are within preparations that are at least 50% by weight (dry weight) the compound of interest. Polypeptides or other compounds described herein are said to be "substantially pure" when they are within preparations that are at least 80% by weight (dry weight) the compound of interest. Polypeptides or other compounds described herein are said to be "homogeneous" when they are within preparations that are at least 95%, and preferably 99%, by weight (dry weight) the compound of interest. Purity is measured by reducing polyacrylamide gel electrophoresis and enhanced coomassie blue staining, followed by optical density traces of bands (i.e., with protein purity being measured through optical densitometry).

"Pyrogen-free" means free of fever causing contaminants, including endotoxin. Measurement of contaminants is to be performed by the applicable standard tests set by the U.S. Food and Drug Administration.

As used herein, the term "therapeutically effective amount" means the total amount of each active component of the relevant pharmaceutical composition or method that is sufficient to show a meaningful patient benefit, i.e., treatment, healing, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

Embodiments of the present invention may be used as intra-articular supplements. Intra-articular supplementation with compounds not derived from lubricin has been practiced as a joint therapy. For example, "viscosupplementation" with polymeric hyaluronan (HA) and higher molecular weight hylans (such as SYNVISC® elastoviscous fluid "Hylan G-F 20"—distributed by WYETH® Pharmaceuticals) is used clinically to treat OA-associated knee pain. This viscosupplementation has shown significant therapeutic value, particularly in reducing weight-bearing pain in patients (Wobig et al., 1998).

Hylan G-F 20 is generated by cross-linking several HA molecules obtained from rooster or chicken combs. Viscosupplementation with Hylan G-F 20 can be significantly more efficacious for alleviating pain than viscosupplementation with lower molecular weight HA (Wobig et al., 1999). In addition, relieving pain by viscosupplementation with Hylan G-F 20 may be particularly preferable to administration of NSAIDs for those patients who do not tolerate NSAIDs (e.g., in patients with a high risk of gastrointestinal complications; Espallargues and Pons, 2003). Though Hylan G-F 20 viscosupplementation is a safe and well-tolerated therapy that provides a short-term (i.e., until 3-6 months posttreatment) decrease in pain symptoms while improving joint function, the therapy may not significantly forestall the eventual need for knee replacement in OA patients (Espallargues and Pons, 2003).

Example 1

Cloning of Recombinant Lubricin

Constructs. In some embodiments, the base DNA construct for the generation of recombinant lubricin molecules is composed of the Met codon (ATG) through the BssHII restriction site (G^CGCGC) of SEQ ID NO: 6 (i.e., base nos. 1 through 1123) and the BspEI restriction site (T^CCGGA) through the stop codon (TAA) of SEQ ID NO: 6 (i.e., base nos. 1269 through 2946). These sequences, i.e., base nos. 1 through 1123 and 1269 through 2946 of SEQ ID NO: 6, encode amino acids M1 through S373 (encoded by exons 1 through 5 and approximately 174 flanking 5'-codons of exon 6) and E848 through P1404 (encoded by approximately 293 flanking 3'-codons of exon 6 and exons 7 through 14) of native full-length lubricin (i.e., PRG4). The portion of exon 6 absent from the base DNA construct corresponds to DNA sequence encoding amino acids A374 through P847 of native PRG4 (474 amino acids absent out of approximately 940 amino acids encoded by exon 6). This absent amino acid sequence is rich in KEPAPTT-like sequences.

DNA sequence of synthetic cDNA cassette-1 (SEQ ID NO: 1) is added BssHII/BspEI to the base construct to make the recombinant PRG4-Lub:1 cDNA construct (SEQ ID NO: 6). SEQ ID NO: 6 is composed of the Lub:1 DNA insert (SEQ ID NO: 8; which encodes the 51 amino acids of SEQ ID NO: 9 with its four KEPAPTT sequences) between DNA encoding amino acids M1 through S373 and DNA encoding E848 through P1404 of native PRG4. In other words, in place of A374 through P847 (474 amino acids) of native PRG4, the recombinant lubricin PRG4-LUB:1 includes 51 amino acids that form four perfect KEPAPTT sequences and approximately three imperfect KEPAPTT sequences.

DNA sequence of synthetic cDNA cassette-2 (SEQ ID NO: 3) is added Bsu36I/BspEI to the PRG4-Lub:1 construct to make the PRG4-Lub:2 cDNA construct (SEQ ID NO: 10). The PRG4-Lub:1 cDNA construct has one Bsu36I restriction site (CC^TNAGG, i.e., CC^TAAGG; base nos. 1225 through 1231 of SEQ ID NO: 6). When synthetic cDNA cassette-2 is added to the PRG4-Lub:1 cDNA construct, this Bsu36I site is destroyed, but synthetic cassette-2 contains another internal Bsu36I restriction site (CC^TNAGG, i.e., CC^TAAGG; base nos. 92 through 98 of SEQ ID NO: 3). Consequently, a PRG4-Lub:N+1 construct can be made by adding synthetic cDNA cassette-2 Bsu36I/BspEI to the previous PRG4-Lub:N construct at this internal Bsu36I restriction site provided by synthetic cDNA cassette-2.

The cDNA cassettes are synthesized as single stranded oligonucleotides and hybridized together to produce a double stranded DNA fragment with sticky ends. This is why the terminal BssHII, Bsu36I, and BspEI sites appear incomplete. In synthetic cDNA cassette-1 (SEQ ID NO: 1), a sequence bounded by remnant flanking BssHII (G^CGCGC) and BspEI (T^CCGGA) restriction sites includes an internal Bsu36I restriction site (CC^TNAGG, i.e., CC^TAAGG); the restriction sites are underlined below:

<u>CGCGCC</u>CACAACTCCAAAAGAGCCCGCACCTACCACGACAAAGTCAGCTC
CTACTACGCCCAAAGAGCCAGCGCCGACGACTACTAAAGAACCGGCACCC
ACCACG<u>CCTAAGG</u>AGCCAGCTCCTACTACAACGAAACCGGCACCAACCAC
<u>TCCGG</u>

SEQ ID NO: 2, which is a translation of SEQ ID NO: 1, includes four KEPAPTT sequences that are perfect matches (highlighted below):

```
 1   A   P   T   T   P   K   E   P   A   P   T   T   T   K   S   A   P   T   T   P
     CGCGCCCACAACTCCAAAAGAGCCCGCACCTACCACGACAAAGTCAGCTCCTACTACGCCC

21   K   E   P   A   P   T   T   T   K   E   P   A   P   T   T   P   K   E   P   A
     AAAGAGCCAGCGCCGACGACTACTAAAGAACCGGCACCCACCACGCCTAAGGAGCCAGCT

41   P   T   T   T   K   P   A   P   T   T   P
     CCTACTACAACGAAACCGGCACCAACCACTCCGG
```

Synthetic cDNA cassette-2 (SEQ ID NO: 3) similarly has a remnant 5'-terminal Bsu36I restriction site (i.e., CC^TNAGG, evidenced only by the TAA sequence), a 3'-terminal remnant BspEI restriction site (T^CCGGA), and an internal Bsu36I restriction site (CC^TNAGG); the restriction sites are underlined below:

<u>TAA</u>AGAACCAGCCCCTACTACGACAAAGGAGCCTGCACCCACAACCACGA

AGAGCGCACCCACAACACCAAAGGAGCCGGCCCCTACGAC<u>TCCTAAGGAA</u>

CCCAAACCGGCACCAACCAC<u>TCCGG</u>

SEQ ID NO: 4, which is a translation of SEQ ID NO: 3, includes three KEPAPTT sequences that are perfect matches (highlighted below):

```
 1   K  E  P  A  P  T  T  T  K  E  P  A  P  T  T  T  K  S  A  P
    TAAAGAACCAGCCCCTACTACGACAAAGGAGCCTGCACCCACAACCACGAAGAGCGCACCC

21   T  T  P  K  E  P  A  P  T  T  P  K  E  P  K  P  A  P  T  T
    ACAACACCAAAGGAGCCGGCCCCTACGACTCCTAAGGAACCCAAACCGGCACCAACCACT

41   P
    CCGG
```

The recombinant PRG4-Lub:1 cDNA construct (SEQ ID NO: 6) in pTmed2 vector (construct plus vector equals SEQ ID NO: 5) is flanked by SalI (G^TCGAC; base nos. 1027 through 1032 of SEQ ID NO: 5) and NotI (GC^GGCCGC; base nos. 3984 through 3991 of SEQ ID NO: 5) restriction sites. The SalI site incorporates a modified Kozak translation initiation sequence (CCCACC; base nos. 1032 through 1037 of SEQ ID NO: 5) before the translation start codon ATG (base nos. 1038 through 1040 of SEQ ID NO: 5). Between the BssHII (G^CGCGC; base nos. 2155 through 2160 of SEQ ID NO: 5) and BspEI (T^CCGGA; base nos. 2306 through 2311 of SEQ ID NO: 5) restriction sites is found the internal Bsu36I cloning site (CC^TNAGG, i.e., CC^TAAGG; base nos. 2262 through 2268 of SEQ ID NO: 5).

The PRG4-Lub:1 cDNA construct (SEQ ID NO: 6) is translated into the PRG4-LUB:1 protein (SEQ ID NO: 7). The insert between S373 and E425 (i.e., E848 of native PRG4) of the entire PRG4-LUB:1 protein (SEQ ID NO: 7) is the 51 amino acids of SEQ ID NO: 9. These are translated from the Lub:1 DNA insert (SEQ ID NO: 8) and include four perfect KEPAPTT sequences. Between the BssHII restriction site (G^CGCGC; base nos. 1118 through 1123 of SEQ ID NO: 6) and the BspEI restriction site (T^CCGGA; base nos. 1269 through 1274 of SEQ ID NO: 6) is found the internal Bsu36I cloning site (CC^TNAGG, i.e., CC^TAAGG; base nos. 1225 through 1231 of SEQ ID NO: 6).

As in the recombinant PRG4-Lub:1 construct in pTmed2 vector, the recombinant PRG4-Lub:2 cDNA construct (SEQ ID NO: 10) in pTmed2 vector is flanked by SalI (G^TCGAC) and NotI (GC^GGCCGC) restriction sites; the SalI site incorporates a modified Kozak translation initiation sequence (CCCACC) before the translation start codon ATG (base nos. 1 through 3 of SEQ ID NO: 10). Similarly, the recombinant PRG4-Lub:3 cDNA construct (SEQ ID NO: 14), the recombinant PRG4-Lub:4 cDNA construct (SEQ ID NO: 18), and the recombinant PRG4-Lub:5 cDNA construct (SEQ ID NO: 22) in pTmed2 vector are each flanked by SalI (G^TCGAC) and NotI (GC^GGCCGC) restriction sites; the SalI site incorporates a modified Kozak translation initiation sequence (CCCACC) before the translation start codon ATG (base nos. 1 through 3 of SEQ ID NOS: 14, 18, and 22, respectively).

Within the PRG4-Lub:2 cDNA construct, the internal Bsu36I cloning site (CC^TNAGG, i.e., CC^TNAGG; base nos. 1318 through 1324 of SEQ ID NO: 10) is found between the BssHII (G^CGCGC; base nos. 11118 through 1123) and BspEI (T^CCGGA; base nos. 1347 through 1352) restriction sites. The PRG4-Lub:2 construct (SEQ ID NO: 10) is translated into the PRG4-LUB:2 protein (SEQ ID NO: 11). The insert between S373 and E451 (i.e., E848 of native PRG4) of the entire PRG4-LUB:2 protein (SEQ ID NO: 11) is the 77 amino acids of SEQ ID NO: 13. These are translated from the Lub:2 DNA insert (SEQ ID NO:12). In place of A374 through P847 (474 amino acids) of native PRG4, the 77 amino acids of the recombinant lubricin PRG4-LUB:2 form six perfect KEPAPTT sequences and approximately four imperfect KEPAPTT sequences.

Within the PRG4-Lub:3 cDNA construct, the internal Bsu36I cloning site (CC^TNAGG, i.e., CC^TAAGG; base nos. 1411 through 1417 of SEQ ID NO: 14) is found between BssHII (G^CGCGC; base nos. 1118 through 1123) and BspEI (T^CCGGA; base nos. 1440 through 1445) restriction sites. The PRG4-Lub:3 construct (SEQ ID NO: 14) is translated into the PRG4-LUB:3 protein (SEQ ID NO: 15). The insert between S373 and E482 (i.e., E848 of native PRG4) of the entire PRG4-LUB:3 protein (SEQ ID NO: 15) is the 108 amino acids of SEQ ID NO: 17. These are translated from the Lub:3 DNA insert (SEQ ID NO:16). In place of A374 through P847 (474 amino acids) of native PRG4, the 108 amino acids of the recombinant lubricin PRG4-LUB:3 form nine perfect KEPAPTT sequences and approximately five imperfect KEPAPTT sequences.

Within the PRG4-Lub:4 cDNA construct, the internal Bsu36I cloning site (CC^TNAGG, i.e., CC^TAAGG; base nos. 1504 through 1510 of SEQ ID NO: 18) is found between BssHII (G^CGCGC; base nos. 1118 through 1123) and BspEI (T^CCGGA; base nos. 1533 through 1538) restriction sites. The PRG4-Lub:4 construct (SEQ ID NO: 18) is translated into the PRG4-LUB:4 protein (SEQ ID NO: 19). The insert between S373 and E513 E848 of native PRG4) of the entire PRG4-LUB:4 protein (SEQ ID NO: 19) is the 139 amino acids of SEQ ID NO: 21. These are translated from the Lub:4 DNA insert (SEQ ID NO:20). In place of A374 through P847 (474 amino acids) of native PRG4, the 139 amino acids of the recombinant lubricin PRG4-LUB:4 form twelve perfect KEPAPTT sequences and approximately six imperfect KEPAPTT sequences.

Within the PRG4-Lub:5 cDNA construct, the internal Bsu36I cloning site (CC^TNAGG, i.e., CC^TAAGG; base nos. 1597 through 1603 of SEQ ID NO: 22) is found between BssHII (G^CGCGC; base nos. 1118 through 1123) and BspEI (T^CCGGA; base nos. 1626 through 1631) restriction sites. The PRG4-Lub:5 construct (SEQ ID NO: 22) is translated into the PRG4-LUB:5 protein (SEQ ID NO: 23). The insert between S373 and E544 (i.e., E848 of native PRG4) of the entire PRG4-LUB:5 protein (SEQ ID NO: 23) is the 170 amino acids of SEQ ID NO: 25. These are translated from the Lub:5 DNA insert (SEQ ID NO:24). In place of A374 through P847 (474 amino acids) of native PRG4, the 170 amino acids of the recombinant lubricin PRG4-LUB:5 form fifteen perfect KEPAPTT sequences and approximately seven imperfect KEPAPTT sequences.

Importantly, the process of inserting the synthetic cDNA cassette-2 can be iterated indefinitely. Each iteration results in the addition of three perfect KEPAPTT sequences. Just as recombinant lubricins PRG4-LUB:2 through PRG4-LUB:5 are constructed in this way through the use of insert sequences, recombinant lubricins PRG4-LUB:6 through PRG4-LUB:N are constructed. Table 2 provides a summary of BssHII/BspE1 insert sequences.

TABLE 2

BssHII|BspE1 Insert Sequences

| LUB INSERT | SEQ ID NO: | Sequences (restriction sites underlined in DNA inserts; KEPAPTT sequences are highlighted in protein inserts) |
| --- | --- | --- |
| Lub: 1 | 8 | GCGCGCCCACAACTCCAAAAGAGCCCGCACCTACCAC GACAAAGTCAGCTCCTACTACGCCCAAAGAGCCAGCG CCGACGACTACTAAAGAACCGGCACCCACCACGCCTA AGGAGCCAGCTCCTACTACAACGAAACCGGCACCAAC CACTCCGGA |
| Lub: 1 | 9 | APTTPKEPAPTTTKSAPTTPKEPAPTTTKEPAPTTPKEPAPTTTKPAPTTP |
| Lub: 2 | 12 | GCGCGCCCACAACTCCAAAAGAGCCCGCACCTACCAC GACAAAGTCAGCTCCTACTACGCCCAAAGAGCCAGCG CCGACGACTACTAAAGAACCGGCACCCACCACGCCTA AGAACCAGCCCCTACTACGACAAAGGAGCCTGCACC CACAACCACGAAGAGCGCACCCACAACACCAAAGGAG CCGGCCCCTACGACTCCTAAGGAACCCAAACCGGCAC CAACCACTCCGGA |
| Lub: 2 | 13 | APTTPKEPAPTTTKSAPTTPKEPAPTTTKEPAPTTPKEPAPTTTKEPAPTTTKSAPTTPKEPAPTTPKEPKPAPTTP |
| Lub: 3 | 16 | GCGCGCCCACAACTCCAAAAGAGCCCGCACCTACCAC GACAAAGTCAGCTCCTACTACGCCCAAAGAGCCAGCG CCGACGACTACTAAAGAACCGGCACCCACCACGCCTA AGAACCAGCCCCTACTACGACAAAGGAGCCTGCACC CACAACCACGAAGAGCGCACCCACAACACCAAAGGAG CCGGCCCCTACGACTCCTAAGGAACCCAAACCCCTACTA CGACAAAGGAGCCTGCACCCACAACCACGAAGAGCGC ACCCACAACACCAAAGGAGCCGGCCCCTACGACTCCT AAGGAACCCAAACCGGCACCAACCACTCCGGA |
| Lub: 3 | 17 | APTTPKEPAPTTTKSAPTTPKEPAPTTTKEPAPTTPKEPAPTTTKEPAPTTTKSAPTTPKEPAPTTPKEPAPTTTKEPAPTTTKSAPTTPKEPAPTTPKEPKPAPTTP |
| Lub: 4 | 20 | GCGCGCCCACAACTCCAAAAGAGCCCGCACCTACCAC GACAAAGTCAGCTCCTACTACGCCCAAAGAGCCAGCG CCGACGACTACTAAAGAACCGGCACCCACCACGCCTA AGAACCAGCCCCTACTACGACAAAGGAGCCTGCACC CACAACCACGAAGAGCGCACCCACAACACCAAAGGAG CCGGCCCCTACGACTCCTAAAGAACCAGCCCCTACTA CGACAAGGAGCCTGCACCCACAACCACGAAGAGCGC ACCCACAACACCAAAGGAGCCGGCCCCTACGACTCCT AAAGAACCAGCCCCTACTACGACAAAGGAGCCTGCAC CCACAACCACGAAGAGCGCACCCACAACACCAAAGGA GCCGGCCCCTACGACTCCTAAGGAACCCAAACCGGCA CCAACCACTCCGGA |
| Lub: 4 | 21 | APTTPKEPAPTTTKSAPTTPKEPAPTTTKEPAPTTPKEPAPTTTKEPAPTTTKSAPTTPKEPAPTTPKEPAPTTTKEPAPTTTKSAPTTPKEPAPTTPKEPAPTTTKEPAPTTTKSAPTTPKEPAPTTPKEPKPSPTTP |
| Lub: 5 | 24 | GCGCGCCCACAACTCCAAAAGAGCCCGCACCTACCAC GACAAAGTCAGCTCCTACTACGCCCAAAGAGCCAGCG CCGACGACTACTAAAGAACCGGCACCCACCACGCCTA AGAACCAGCCCCTACTACGACAAAGGAGCCTGCACC |

TABLE 2-continued

BssHII|BspE1 Insert Sequences

| LUB INSERT | SEQ ID NO: | Sequences (restriction sites underlined in DNA inserts; KEPAPTT sequences are highlighted in protein inserts) |
| --- | --- | --- |
| | | CACAACCACGAAGAGCGCACCCACAACACCAAAGGAG CCGGCCCCTACGACTCCTAAAGAACCAGCCCCTACTA CGACAAAGGAGCCTGCACCCACAACCACGAAGAGCGC ACCCACAACACCAAAGGAGCCGGCCCCTACGACTCCT AAAGAACCAGCCCCTACTACGACAAAGGAGCCTGCAC CCACAACCACGAAGAGCGCACCCACAACACCAAAGGA GCCGGCCCCTACGACTCCTAAAGAACCAGCCCCTACT ACGACAAAGGAGCCTGCACCCACAACCACGAAGAGCG CACCCACAACACCAAAGGAGCCGGCCCCTACGACTCC TAAGGAACCCAAACCGGCACCAACCACTCCGGA |
| LUB: 5 | 25 | APTTPKEPAPTTTKSAPTTPKEPAPTTTKEPAPTTPKEPAPTTTKEPAPTTTKSAPTTPKEPAPTTPKEPAPTTTKEPAPTTTKSAPTTPKEPAPTTPKEPAPTTTKEPAPTTTKSAPTTPKEPAPTTPKEPAPTTTKEPAPTTTKSAPTTPKEPAPTTPKEPKPAPTTP |

Although we have exemplified the base DNA construct with full-length PRG4 containing all 12 exons (minus a central portion of exon 6), splice variants of PRG4 may also be employed, depending on the various activities and length desired. Additionally, different restrictions enzymes may be employed in an analogous strategy, providing that their location is conveniently located within nucleic acid sequence encoding PRG4 protein. In other embodiments, the base DNA construct lacks native exon 6 sequence, but includes one or more of exon 1 through exon 5 sequences or of exon 7 through exon 12 sequences of the native PRG4 gene. In other embodiments, the base DNA construct is identical to a recombinant MSF sequences described in U.S. Pat. No. 6,433,142 or US20020137894 except that part or all of the sequences of exon 6 are absent.

The invention provides cDNA constructs encoding recombinant lubricins that are cloned into SalI (G^TCGAC; base nos. 1027 through 1032 of SEQ ID NO: 5) and NotI (GC^GGCCGC; base nos. 3984 through 3991 of SEQ ID NO: 5) restriction sites in the eucaryotic expression vector pTmed2 as a preferred embodiment (e.g., recombinant PRG4-Lub:1 cDNA construct in pTmed2 expression vector is located in SEQ ID NO: 5 at base nos. 1038 though 3983). The SalI site incorporates the first base of a modified Kozak translation initiation sequence (CCCACC; base no. 1032 of SEQ ID NO: 5) before the methionine start codon (ATG; base nos. 1038 through 1040 of SEQ ID NO: 5). Other embodiments of the invention include other restriction site combinations and other expression vectors.

In a preferred embodiment, the interative process makes use of the synthetic cDNA cassette-1 (SEQ ID NO: 1) in expression vector pTmed2, which is flanked by the restriction sites for BssHII (G^CGCGC) and BspEI (T^CCGGA), and the synthetic cDNA cassette-1, which includes an internal Bsu36I restriction site (CC^TNAGG, i.e., CC^TAAGG; base nos. 107 to 113 of SEQ ID NO: 1). For the iterative generation of recombinant lubricin constructs containing KEPAPTT-like sequences in this preferred embodiment, synthetic cDNA cassette-2 (SEQ ID NO: 3) is inserted between the Bsu36I and BspEI sites of the recombinant construct. Synthetic cDNA cassette-2 (SEQ ID NO: 3) is flanked by a modified remnant Bsu36I site (TAAAG) and a remnant BspEI (ACTCCGG) site. It also includes an internal Bsu36I site (CC^TNAGG, i.e., CC^TAAGG; base nos. 92 through 98 of SEQ ID NO: 3).

Upon cloning synthetic cDNA cassette-2 into the Bsu36I and BspEI sites of a recombinant lubricin construct, the Bsu36I cloning site of the original construct is destroyed leaving one unique Bsu36I cloning site in the new construct.

In this preferred embodiment, the amino acid sequence "APTTPKEPAPTT TKSAPTTPKEPAPTTTKEPAPTTP KEPAPTTTK" (SEQ ID NO: 26; 45 amino acids) remains a part of each PRG4-LUB:N protein (where N=an integer of 1 or more). In addition, the amino acid sequence "KEPAPTTT KEPAPTTTKSAPTTPKEPAPTTP" (SEQ ID NO: 27; 31 amino acids) is encoded by the DNA insert that becomes part of each PRG4-Lub:N+1 cDNA construct through the addition of synthetic cDNA cassette-2 Bsu36I/BspEI to a PRG4-Lub:N cDNA construct. For PRG4-LUB:N protein where N is an integer greater than or equal to 3, the amino acid sequence "EPAPTTTKSAPTTPKEPAPTTP" (SEQ ID NO: 28; 22 amino acids) joins SEQ ID NO: 26 to (N minus 2) repeats of SEQ ID NO: 27 in preferred embodiments. Furthermore, the amino acid sequence "KEPKPAPTTP" (SEQ ID NO: 29; 10 amino acids) immediately follows the last insert repeat of SEQ ID NO: 27 in preferred embodiments of the PRG4-LUB:N protein where N is an integer greater than or equal to 2.

Because they form at least two KEPAPTT sequences, SEQ ID NO: 26, SEQ ID NO: 27, and SEQ ID NO: 28 are each designated herein to be a "repetitive KEPAPTT-like sequence" (the N-terminus of SEQ ID 28 links to a K residue so that SEQ ID NO: 28 forms two KEPAPTT sequences in PRG4-LUB:N proteins).

Consequently, for recombinant lubricin protein PRG4-LUB:N (where N equals an integer of 1 or more), the PRG4-LUB:N protein comprises SEQ ID NO: 26 in a preferred embodiment. Furthermore, for recombinant lubricin protein PRG4-LUB:N (where N equals an integer of 2 or more), the PRG4-LUB:N protein also comprises SEQ ID NO: 27 in a preferred embodiment. SEQ ID NO: 27 is repeated (N minus 1) times within each PRG4-LUB:N protein in these preferred embodiments. In PRG4-LUB:2, SEQ ID NO: 26 and SEQ ID NO: 27 overlap (i.e., they share a KEPAPTT sequence).

In other preferred embodiments where N is an integer greater than or equal to 3 (e.g., where N equals an integer from 3 through 200, or in more preferred embodiments where N equals an integer from 5 through 50, or in even more preferred embodiments where N equals an integer from 10 through 30), recombinant lubricin protein comprises the 22 amino acids of SEQ ID NO: 28 joining the N-terminal-oriented 45 amino acids of SEQ ID NO: 26 to (N minus 2) repeat(s) of the 31 amino acids of SEQ ID NO: 27, where the 10 amino acids of SEQ ID NO: 29 are C-terminal to the last 31-amino-acid repeat of SEQ ID NO: 27.

TABLE 3

Sequence Frequencies in Preferred PRG4-LUB Proteins

| PRG4-LUB Protein | SEQ ID NO: 26 N-end insert | SEQ ID NO: 28 >--< | SEQ ID NO: 27 >--< | SEQ ID NO: 29 insert C-end | KEPAPTT repeats |
|---|---|---|---|---|---|
| -LUB:1 | 1 | 0 | 0 | 0 | 4 |
| -LUB:2 | 1 | 0 | 1 | 1 | 6 |
| -LUB:3 | 1 | 1 | 1 | 1 | 9 |
| -LUB:4 | 1 | 1 | 2 | 1 | 12 |
| -LUB:5 | 1 | 1 | 3 | 1 | 15 |
| -LUB:N | 1 | 1 | N-2 | 1 | 3 × N |

PRG4-LUB:N proteins in general have (3 times N) repeats of the KEPAPTT sequence in preferred embodiments where N equals the number of repetitive KEPAPTT-like sequences.

Recombinant lubricin PRG4-LUB:5 (having 3×N=3×5=15 copies of the KEPAPTT sequence in preferred embodiments) is the largest recombinant lubricin PRG4-LUB:N whose sequence is detailed herein. For recombinant lubricin of the present invention, however, the value N may be greater than 5, such as 7, 10, 12, 15, 20, 25, 30, 40, 50, 100, 150, 200 or more.

In particular, proteins PRG4-LUB:1, PRG4-LUB:2, PRG4-LUB:3, PRG4-LUB:4, and PRG4-LUB:5 are detailed herein with 4, 6, 9, 12 and 15 perfect KEPAPTT sequences, respectively. However, it is possible to add increasing numbers of KEPAPTT sequences by continuing the iterative Lub:N insert procedure described herein. We have provided detailed description for PRG4-LUB:N recombinant lubricins with relatively low numbers of KEPAPTT or KEPAPTT-like sequences as compared with native PRG4/lubricin protein because smaller proteins are easier to synthesize and manipulate.

It may also be desirable to increase the number of KEPAPTT-like sequences over that seen in native PRG4 protein. This can be accomplished either by continuing the iterative Lub:N insert procedure described herein so that there are more than 78 KEPAPTT-like sequences in the recombinant lubricin PRG4-LUB:N protein, or by beginning with an intact PRG4 cDNA, rather than an exon 6-deleted or an exon 6-diminished version of PRG4 cDNA. Thus any KEPAPTT-like sequences added will be in excess of the number found in native PRG4 protein. Insert procedures used for the generation of larger recombinant lubricin proteins from an intact PRG4 cDNA, as well as insert procedures that use an exon 6-deleted or an exon 6-diminished version of PRG4 cDNA, are encompassed within the invention.

Example 2

Expression and Purification of 'Lub' Protein

PRG4-Lub:1 cDNA construct (SEQ ID NO: 6; containing synthetic cDNA cassette-1 sequence) was expressed in a stably transfected, preadaptive CHO DUKX cell line, purified from conditioned media, and solubilized in PBS containing 500 mM L-arginine hydrochloride as follows.

The PRG4-Lub:1 cDNA construct was expressed in a stably transfected CHO DUKX cell line and the conditioned media was collected. A two liter volume of this conditioned media was filter concentrated under compressed nitrogen gas (40 psi) using an AMICON® M2000™ filtration unit fitted with either a 10 kDa nominal molecular weight limit (NMWL), a 30 kDa NMWL or a 100 kDa NMWL PALL FILTRON® OMEGA™ disc membrane. Media was concentrated to approximately a 100 ml volume, which was aspirated from the disc membrane. The disc membrane was then removed from the AMICON® M2000 filtration unit. The "mucinous" retentate, which had accumulated at the surface of the disc membrane, was harvested using a cell scraper and transferred to microcentrifuge tubes. The samples in the microcentrifuge tubes were centrifuged at approximately 12,000×g for 10 minutes, and the aqueous supernatant was removed. The remaining "lubricin-enriched" pellets were dissolved in phosphate buffered saline (PBS) containing 500 mM L-arginine hydrochloride. The L-arginine hydrochloride concentration may range from 100 mM to 2.0 M.

Using the above procedure, PRG4-LUB:2 through PRG4-LUB:5 glycoproteins (and PRG4-LUB:N proteins where N=a nonnegative integer of 6 or more, as well as other glycoproteins containing KEPAPTT-like sequences) are harvested directly from disc membranes, i.e., without purification of the concentrate remaining above disc membranes.

That is, these recombinant lubricin glycoproteins are isolated directly from disc membranes of 10 kDa NMWL, 30 kDa NMWL, or 100 kDa NMWL PALL FILTRON® OMEGA™ filtration units. In some instances, these glycoproteins may also be purified from the concentrate remaining above disc membranes through chromatographic techniques or electrophoretic techniques or both. Recombinant lubricin proteins and glycoproteins may also be purified using chromatography and other techniques known in the art (as, for example, described in U.S. Pat. No. 6,433,142 for MSF proteins; see also: Deutscher, 1990; and Scopes, 1994).

Example 3

Immunohistochemistry

The cell source of lubricin in normal and osteoarthritic joints was further investigated using immunohistochemical techniques. In addition, the presence of lubricin on other tissue surfaces, including pleura, pericardium, peritoneum, and meninges, was examined according to the following methods.

Osteoarthritic cartilage and synovium were obtained by informed consent from patients undergoing knee replacement surgery. Other tissues examined were normal human synovium and normal non-human primate (NHP) synovium, cartilage, pleura, pericardium, peritoneum, meninges, brain, tendon, and ligaments, and canine normal and osteoarthritic meniscus, cartilage, synovium, ligament, and tendons. Tissues were fixed in 4% paraformaldehyde immediately after harvest or following 24 hours incubation in media without and with supplemental monensin (5 µM). For immunohistochemical studies the tissues were fixed in 4% paraformaldehyde for 24 hours and 6-8 micron paraffin sections were obtained. A subset of tissues were frozen in optical coherence tomography (OCT) freezing compound and cut at 5 to 10 micron intervals followed by acetone fixation.

Immunohistochemical and immunofluorescent analyses utilized a purified polyclonal rabbit anti-human lubricin antibody (Ab 06A10) generated by immunization with a truncated form of recombinant lubricin and purification on a protein A column. CD16 antibody (NEOMARKERS®, Fremont Calif.) was used to identify macrophages (Fcy receptor III). CD106/VCAM-1 antibody (NEOMARKERS®) was used to label fibroblasts within cryostat sections. For control sections, an equivalent concentration of RIgG (VECTOR LABS™, CA), MIgG$_1$ (DAKO®), and MIgG$_{2a}$ (DAKO®) was used consecutively. The Dextran Technology System (ENVISION+™; DAKO®) was used to visualize antibody binding and the sections were counterstained with Mayer's alum-hematoxylin. Immunofluorescence was performed using the above primary antibodies and probed with secondary antibodies (Alexa Dyes—MOLECULAR PROBE™, Oregon) goat anti-rabbit Alexa dye at 546 nm and goat anti-mouse Alexa dye at 488 nm. Fluorescent binding of the antibody was detected with a NIKON® fluorescent microscope.

Lubricin was detected along the surfaces of normal and osteoarthritic human articular cartilage and synovium. A thick layer of lubricin completely coated the fibrillated osteoarthritic surface. CD106 immunofluorescence showed strong cell membrane staining of the intimal fibroblasts of the synovium; lubricin protein was also visualized as staining within synovial cells. Double immunostaining for CD106+ lubricin, clearly showed co-localization within the intimal fibroblasts of the synovium. CD16 staining of synovial macrophages demonstrated the presence of these cells throughout the layers of the synovium, but there was no co-localization with lubricin.

Staining of NHP and canine articular tissues (normal and OA) with the lubricin antibody showed lubricin coating the surface layer of the synovium, cartilage, meniscus, and tendons. NHP cartilage also showed strong immunoreactivity not only in the superficial zone cells but also the transitional zone cells without the addition of monensin to increase intracellular stores of the glycoprotein. Cells lining the peritoneum, pericardium, and pleura also exhibited lubricin expression, though no immunoreactivity was observed in the meninges or brain.

In summary, both normal and osteoarthritic synovium, tendon, meniscus and cartilage were coated by a substantial layer of lubricin. The glycoprotein is clearly present on tissues within OA joints. Double-immunofluorescent staining of human OA synovium demonstrated that the intimal fibroblast synoviocytes were responsible for the synthesis of lubricin.

The localization of lubricin protein outside joint tissue has not been previously described. A surface layer of lubricin was clearly demonstrated on lung pleura, pericardium, and peritoneum. Lubricin is reputed to have a lubricating function within the synovial joint, but may have multiple roles including, but not limited to, lubrication and anti-adhesive functions in other tissues. Supplementation of these other tissues with lubricin is a biotherapy encompassed within this invention.

Example 4

Recombinant Lubricin as a Mechanical Lubricant

Recombinant lubricin could be used as a lubricant generally, e.g., with seals and bearings and the like. For example, U.S. Pat. No. 3,973,781 entitled "Self-lubricating seal," U.S. Pat. No. 4,491,331 entitled "Grooved mechanical face seal," U.S. Pat. No. 4,560,174 entitled "Multi lip seal," and U.S. Pat. No. 4,973,068 entitled "Differential surface roughness dynamic seals and bearings," each describe seals of varying designs. Recombinant lubricin could be used as a lubricant with these seals.

In particular, recombinant lubricin could be used as a lubricant for medical devices, prostheses, and implants, particularly where a biocompatible lubricant is required. In addition, the applications need not be medical, but could include applications in environmentally sensitive contexts where a biocompatible lubricant may be desirable.

Example 5

Recombinant Lubricin Compositions

A recombinant lubricin of the present invention may be used in a pharmaceutical composition when combined with a pharmaceutically acceptable carrier. Such a composition may also contain (in addition to protein and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain cytokines, lymphokines, or other hematopoietic factors such as M-CSF, GM-CSF, TNF, IL-1, IL-2, IL-3, IL4, IL-5, IL-6, IL-7, IL-8, IL-9, IL-10, IL-11, IL-12, IL-13, IL-14, IL-15, TNF1, TNF2, G-CSF, Meg-CSF, thrombopoietin, stem cell factor, and erythropoietin. The pharmaceutical composition may further contain other agents which either enhance the activity of the protein or complement its activity or use in treatment. Such additional factors and/or agents may be included in the pharmaceutical composition to produce a synergistic effect with protein of the invention, or to minimize side effects. Conversely, protein of the present invention may be included in formulations of the particular cytokine, lymphokine, other hematopoietic factor, thrombolytic or anti-thrombotic factor, or anti-inflammatory agent to minimize side effects.

Use of recombinant lubricin protein for intra-articular supplementation in combination with the previously described polymeric hyaluronan (HA) and higher molecular weight hylans is particularly preferred. Other preferred combinations for use in intra-articular supplementation include the use of recombinant lubricin protein with anesthetics (e.g., lidocaine), steroids (e.g., triamcinolone hexacetonide), or radioisotopes (e.g., yttrium). Other preferred combinations for use in intra-articular supplementation may include autologous or heterologous cell preparations (e.g., of cultured chondrocytes, synoviocytes, or stem cells, whether autologously or heterologously derived).

A recombinant lubricin of the present invention may be active in multimers (e.g., heterodimers or homodimers) or complexes with itself or other proteins. As a result, pharmaceutical compositions of the invention may comprise a protein of the invention in such multimeric or complexed form.

A pharmaceutical composition of the invention may be in the form of a complex of the recombinant lubricin protein(s) of present invention along with protein or peptide antigens. The protein and/or peptide antigen will deliver a stimulatory signal to both B and T lymphocytes. B lymphocytes will respond to antigen through their surface immunoglobulin receptor. T lymphocytes will respond to antigen through the T cell receptor (TCR) following presentation of the antigen by MHC proteins. MHC and structurally related proteins including those encoded by class I and class II MHC genes on host cells will serve to present the peptide antigen(s) to T lymphocytes. The antigen components could also be supplied as purified MHC-peptide complexes alone or with co-stimulatory molecules that can directly signal T cells. Alternatively antibodies able to bind surface immunoglobulin and other molecules on B cells as well as antibodies able to bind the TCR and other molecules on T cells can be combined with the pharmaceutical composition of the invention.

A pharmaceutical composition of the invention may be in the form of a liposome in which protein of the present invention is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871, U.S. Pat. No. 4,501,728, U.S. Pat. No. 4,837,028, and U.S. Pat. No. 4,737,323.

In practicing the method of treatment or use of the present invention, a therapeutically effective amount of protein of the present invention is administered to a subject (e.g., a mammal) having a condition to be treated. Protein of the present invention may be administered in accordance with the method of the invention either alone or in combination with other therapies such as treatments employing cytokines, lymphokines, other hematopoietic factors, or cell-based supplements. When co-administered with one or more cytokines, lymphokines, other hematopoietic factors, or cell-based supplements, protein of the present invention may be administered either simultaneously with the cytokine(s), lymphokine(s), other hematopoietic factor(s), thrombolytic or antithrombotic factors, or cell-based supplement, or sequentially. If administered sequentially, the attending physician will decide on the appropriate sequence of administering protein of the present invention in combination with cytokine(s), lymphokine(s), other hematopoietic factor(s), thrombolytic or anti-thrombotic factors, or cell-based supplement.

Administration of protein of the present invention used in the pharmaceutical composition or to practice the method of the present invention can be carried out in a variety of conventional ways, such as cutaneous, subcutaneous, intraperitoneal, parenteral or intravenous injection, or, in some instances, oral ingestion, inhalation, topical application. Administration to a patient by injection into joint tissue is generally preferred (Schumacher, 2003).

When a therapeutically effective amount of protein of the present invention is administered orally, protein of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% protein of the present invention, and preferably from about 25 to 90% protein of the present invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of protein of the present invention, and preferably from about 1 to 50% protein of the present invention.

When a therapeutically effective amount of protein of the present invention is administered by intravenous, cutaneous or subcutaneous injection, protein of the present invention will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to protein of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art. For example, injection in association with, or in combination with, lidocaine or other local anesthetic, steroids or adrenocorticoids, HA and/or hylans, or radioisotopes are all encompassed within by the present invention.

The amount of protein of the present invention in the pharmaceutical composition of the present invention will depend upon the nature and severity of the condition being treated, and on the nature of prior treatments which the patient has undergone. Ultimately, the attending physician will decide the amount of protein of the present invention with which to treat each individual patient. Initially, the attending physician will administer low doses of protein of the present invention and observe the patient's response. Larger doses of protein of the present invention may be administered until the optimal therapeutic effect is obtained for the patient, and at that point the dosage is not increased further. It is contemplated that the various pharmaceutical compositions used to practice the method of the present invention should contain about 0.01 μg to about 100 mg (preferably about 0.1 μg to about 10 mg, more preferably about 0.1 μg to about 1 mg) of protein of the present invention per kg body weight depending on the method of administration and the exact therapeutic course implemented.

If administered intravenously, the duration of intravenous therapy using a pharmaceutical composition comprising recombinant lubricin of the present invention will vary, depending on the severity of the disease being treated and the condition and potential idiosyncratic response of each individual patient. It is contemplated that the duration of each application of the protein of the present invention may be in the range of 12 to 24 hours of continuous intravenous administration. Ultimately the attending physician will decide on the appropriate duration of intravenous therapy using the pharmaceutical composition of the present invention.

For compositions of the present invention which are useful for bone, cartilage, tendon or ligament therapy, the therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or tissue damage. Topical administration may be suitable for in some wound healing and tissue repair contexts. Therapeutically useful agents which may also optionally be included in the composition as described above, may alternatively or additionally, be administered simultaneously or sequentially with the composition comprising recombinant lubricin protein of the invention in the methods of the invention. Preferably the composition would include a matrix capable of delivering the protein-containing composition to the site of bone and/or cartilage damage, possibly capable of providing a structure for the developing bone and cartilage, and optimally capable of being resorbed into the body. Such matrices may be formed of materials presently in use for other implanted medical applications.

If a matrix is used, the choice of matrix material is based on biocompatibility, biodegradability, mechanical properties, cosmetic appearance and interface properties. The particular application of the compositions will define the appropriate formulation. Potential matrices for the compositions may be biodegradable and chemically defined calcium sulfate, tricalciumphosphate, hydroxyapatite, polylactic acid, polyglycolic acid and polyanhydrides. Other potential materials are biodegradable and biologically well-defined, such as bone or dermal collagen. Further matrices are comprised of pure proteins or extracellular matrix components. Other potential matrices are nonbiodegradable and chemically defined, such as sintered hydroxapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

In further compositions, proteins of the invention may be combined with other agents beneficial to the treatment of the bone and/or cartilage defect, wound, or tissue in question. These agents include various growth factors such as epidermal growth factor (EGF), platelet derived growth factor (PDGF), transforming growth factors (TGF-α and TGF-β), and insulin-like growth factor (IGF).

The therapeutic compositions are also presently valuable for veterinary applications. Particularly domestic animals such as cats and dogs, laboratory animals such as mice and rats, as well as horses, in addition to humans, are particularly desired subjects or patients for such treatment with recombinant lubricin proteins of the present invention.

The dosage regimen of a protein-containing pharmaceutical composition to be used in tissue regeneration will be determined by the attending physician considering various factors which modify the action of the proteins, e.g., amount of tissue weight desired to be formed, the site of damage, the condition of the damaged tissue, the size of a wound, type of damaged tissue (e.g., cartilage or tendon), the patient's age, sex, and diet, the severity of any infection, time of administration and other clinical factors. The dosage may vary with the type of matrix used in the reconstitution and with inclusion of other proteins in the pharmaceutical composition. For example, the addition of other known growth factors, such as IGF I (insulin like growth factor I), to the final composition, may also effect the dosage. Progress can be monitored by periodic assessment of tissue/bone growth and/or repair, for example, X-rays, histomorphometric determinations and tetracycline labeling.

Polynucleotides of the present invention can also be used for gene therapy. Such polynucleotides can be introduced either in vivo or ex vivo into cells for expression in a subject (e.g., a mammal). Polynucleotides of the invention may also be administered by other known methods for introduction of nucleic acid into a cell or organism (including, without limitation, in the form of viral vectors or naked DNA).

Cells may also be cultured ex vivo in the presence of nucleic acids or proteins of the present invention in order to proliferate or to produce a desired effect on or activity in such cells. Treated cells can then be introduced in vivo for therapeutic purposes.

Example 6

Anti-Lubricin Antibodies

Recombinant lubricin protein of the invention may also be used to immunize animals to obtain polyclonal and monoclonal antibodies which specifically react with the protein or, in some embodiments, its native counterparts. Such antibodies may be obtained using either complete recombinant lubricin protein or fragments thereof as an immunogen. The peptide immunogens additionally may contain a cysteine residue at the carboxyl terminus, and are conjugated to a hapten such as keyhole limpet hemocyanin (KLH). Methods for synthesizing such peptides are known in the art (for example, as in Merrifield, 1963; and Krstenansky et al., 1987). Monoclonal antibodies binding to recombinant lubricin protein of the invention may be useful diagnostic agents for the immunodetection of related proteins. Neutralizing monoclonal antibodies binding to these related proteins may also be useful therapeutics for both conditions associated with lubricin or, in some cases, in the treatment of some forms of cancer where abnormal expression of lubricin may be involved (e.g., in synoviomas).

In addition to antibodies which are directed to the polypeptide core of a recombinant lubricin protein, an antibody directed to a sugar portion or to a glycoprotein complex of recombinant lubricin protein is desirable. In order to generate antibodies which bind to glycosylated recombinant lubricin (but not to a deglycosylated form), the immunogen is preferably a glycopeptide, the amino acid sequence of which spans a highly glycosylated portion of the recombinant lubricin, e.g., a repetitive KEPAPTT-like sequence. Shorter glycopeptides, e.g., 8-15 amino acids in length, within the same highly glycosylated region, are also used as immunogens. Methods of generating antibodies to highly glycosylated biomolecules are known in the art (for example, as described by Schneerson et al., 1980).

Example 7

Recombinant Lubricin Delivery

Standard methods for delivery of recombinant lubricin are used. For intra-articular administration, recombinant lubricin is delivered to the synovial cavity at a concentration in the range of 20-500 µg/ml in a volume of approximately 0.1-2 ml per injection. For example, 1 ml of a recombinant lubricin at a concentration of 200-300 µg/ml is injected into a knee joint using a fine (e.g., 14-30 gauge, preferably 18-26 gauge) needle. The compositions of the invention are also useful for parenteral administration, such as intravenous, subcutaneous, intramuscular, or intraperitoneal administration, and, in preferred embodiments, onto the surfaces of the peritoneal, pericardium, or pleura.

Proper needle placement is critical for the efficacy of recombinant lubricin protein that is delivered by injection in joint therapies (Schumacher, 2003). Proper needle placement may be facilitated through the use of ultrasound technology. Successful injections are more common after successful aspiration of fluid is obtained. A supralateral approach into the suprapatellar pouch has been suggested to provide the most reliable access to knee joint space. In addition to administering recombinant lubricin by intra-articular injection, nucleic acids encoding recombinant lubricin (e.g., in gene therapy applications) may be administered to a synovial cavity by intra-articular injection.

For prevention of surgical adhesions, recombinant lubricins described herein are administered in the form of gel, foam, fiber or fabric. A recombinant lubricin formulated in such a manner is placed over and between damaged or exposed tissue interfaces in order to prevent adhesion formation between apposing surfaces. To be effective, the gel or film must remain in place and prevent tissue contact for a long enough time so that when the gel finally disperses and the tissues do come into contact, they will no longer have a tendency to adhere. Recombinant lubricin formulated for inhibition or prevention of adhesion formation (e.g., in the form of a membrane, fabric, foam, or gel) are evaluated for prevention of post-surgical adhesions in a rat cecal abrasion model (Goldberg et al., 1993). Compositions are placed around surgically abraded rat ceca, and compared to non-treated controls (animals whose ceca were abraded but did not receive any treatment). A reduction in the amount of adhesion formation in the rat model in the presence of recombinant lubricin formulation compared to the amount in the absence of the formulation indicates that the formulation is clinically effective to reduce tissue adhesion formation. In contexts where tissue adhesion is desired (e.g., where healing of cartilage fissures is desired), however, use of recombinant lubricin may be best avoided. Providing lubrication to cartilage surfaces impairs cartilage-cartilage integration (Schaefer et al., 2004).

Recombinant lubricins are also used to coat artificial limbs and joints prior to implantation into a mammal. For example, such devices may be dipped or bathed in a solution of a recombinant lubricin, e.g., following methods described in U.S. Pat. No. 5,709,020 or U.S. Pat. No. 5,702,456. Care should be exercised, however, in the in vivo use of recombinant lubricin in providing lubrication near a prostheses. A marked upregulation in PRG4 gene expression (i.e., MSF gene expression) has been reported to be associated with prosthesis loosening; lubricin could disturb the tight interaction between bone and prosthesis and thereby contribute to prosthesis loosening (Morawietz et al., 2003).

Example 8

OA Model

In order to assess the efficacy of intra-articular administration of lubricin preparations, a murine model of osteoarthritis/cartilage erosion is prepared. For surgical induction of osteoarthritis, mice are anesthetized with 250 mg/kg intraperitoneal tribromoethanol (SIGMA® Chemical), and knees are prepared for aseptic surgery. A longitudinal incision medial to the patellar ligament is made, the joint capsule is opened, and the meniscotibial ligament (anchoring the medial meniscus to the tibial plateau) is identified. In a subset of animals, no further manipulation is performed, and this group is considered sham operated. In the experimental group the medial meniscotibial ligament is transected resulting in destabilization of the medial meniscus (DMM). In both sham and DMM animals, the joint capsule and subcutaneous layer are sutured closed separately and the skin is closed by application of NEXABAND® S/C tissue adhesive (Abbott, North Chicago, Ill.). Buprenorphine (BUPRENEX®; Reckitt & Coleman, Kingston-upon-Hull, UK) is administered pre- and post-operatively.

Recombinant lubricin preparations are administered by intra-articular injection using a 30 gauge needle. Injections of 5-10 microliters per knee joint are administered one week post surgery. Additional injections are optionally administered on a weekly basis. Animals are sacrificed by carbon dioxide at 4 weeks post-operatively and at 8 weeks post-operatively.

In order to assess the progression and severity of osteoarthritis, intact knee joints are placed into 4% paraformaldehyde for 24 hours, then decalcified in EDTA/polyvinylpyrrolidone for five days. Joints are embedded in paraffin and 6-µm frontal sections obtained through the entire joint. Slides are stained with Safranin O-fast green and graded at 70-µm intervals through the joint using a modification of a semi-quantitative scoring system (Chambers et al., 2001) in which "0"=normal cartilage; "0.5"=loss of Safranin O without structural changes; "1"=roughened articular surface and small fibrillations; "2"=fibrillation down to the layer immediately below the superficial layer and some loss of surface lamina; "3"=mild (<20%); "5"=moderate (20-80%); and "6"=severe (>80%) loss of non-calcified cartilage. Scores of "4" (erosion to bone) are not a feature of this model. All quadrants of the joint (medial tibial plateau, medial femoral condyle, lateral tibial plateau, and lateral femoral condyle) are scored separately. A minimum of 12 levels are scored by blinded observers for each knee joint. Scores are expressed as the maximum histologic score found in each joint or the summed histologic scores. The summed score represents the additive scores for each quadrant of the joint on each histologic section through the joint. This method of analysis enables assessment of severity of lesions as well as the surface area of cartilage affected with OA-like lesions (Glasson et al., 2004).

References: (1) Chambers et al., 2001, *Arthritis Rheum.* 44: 1455-65; (2) Deutscher, 1990, *Methods in Enzymology, Vol. 182: Guide to Protein Purification*, Academic Press; (3) Espallargues and Pons, 2003, *Int'l J. Tech. Assess. Health Care* 19: 41-56; (4) Flannery et al., 1999, *Biochem. Biophys. Res. Comm.* 254: 535-41; (5) Glasson et al., 2004, *Arthritis Rheum.* 50: 2547-58; (6) Goldberg et al., 1993, In: *Gyneco-* logic Surgery and Adhesion Prevention, Willey-Liss, pp. 191-204; (7) Hills, 2002, *J. Rheumatology* 29: 200-01; (8) Ikegawa et al., 2000, *Cytogenet. Cell Genet.* 90: 291-297; (9) Jay et al., 2001, *J. Orthopaedic Research* 19: 677-87; (10) Jay et al., 2002, *Glycoconjugate Journal* 18: 807-15; (11) Krstenansky et al., 1987, *FEBS Lett.* 211: 10-16; (12) Marcelino et al., 1999, *Nature Genetics* 23: 319-322; (13) Merberg et al., 1993, *Biology of Vitronectins and their Receptors*, Pressner et al. (eds.): Elsevier Science Publishers, pp. 45-53; (14) Merrifield, 1963, *J. Amer. Chem. Soc.* 85: 2149-54; (15) Morawietz et al., 2003, *Virchows Arch.* 443: 57-66; (16) Rees et al., 2002, *Matrix Biology* 21: 593-602; (17) Schneerson et al., 1980, *J. Exp. Med.* 152: 361-76; (18) Scopes, 1994, *Protein Purification: Principles and Practice* (3$^{rd}$ edition), Springer Verlag; (19) Schaefer et al., 2004, *Biorheology* 41: 503-508; (20) Schumacher, 2003, *Arthritis & Rheumatism* 49: 413-20; (21) Tatusova and Madden, 1999, *FEMS Microbiol Lett.* 174: 247-50; (22) Wobig et al., 1998, *Clin. Ther.* 20: 410-23; and (23) Wobig et al., 1999, *Clin. Ther.* 21: 1549-62.

We claim:

1. An isolated protein comprising the polypeptide of SEQ ID NO: 11.

2. The protein of claim 1, wherein the protein is O-linked to β-(1-3)-Gal-GalNac.

3. A composition comprising a therapeutically effective amount of the protein of claim 2 in a pharmaceutically acceptable carrier.

4. The composition of claim 3, additionally comprising hyaluronan or hylan.

5. The composition of claim 3, wherein the composition is formulated for injection.

6. The composition of claim 3, wherein the composition is encapsulated.

7. The composition of claim 6, wherein the composition is encapsulated in an implantable drug delivery matrix.

8. The composition of claim 3, wherein the composition further comprises a local anesthetic.

9. The composition of claim 3, wherein the composition further comprises a cytokine.

10. The composition of claim 3, wherein the composition further comprises a lymphokine.

11. The composition of claim 3, wherein the composition further comprises a thrombolytic factor.

12. The composition of claim 3, wherein the composition further comprises an antithrombolytic factor.

13. The composition of claim 3, wherein the composition further comprises an anti-inflammatory agent.

14. The composition of claim 3, wherein the composition further comprises an antibiotic.

15. The composition of claim 3, wherein the composition further comprises a growth factor.

16. A method of enhancing the lubrication of a tissue of a subject in need thereof, comprising administering to the tissue of the subject the composition of claim 3, wherein the tissue is lubricated.

17. The method of claim 16, wherein the tissue is selected from the group consisting of cartilage, synovium, meniscus, tendon, lung pleura, pericardium, and peritoneum.

18. A method of countering undesired adhesion between tissues in a subject in need thereof, comprising administering to at least one tissue of the subject the composition of claim 3, wherein the undesired adhesion between the tissues is countered.

19. A method for lubricating the surface of a tissue of a subject in need thereof, comprising administering to the tissue of the subject the composition of claim 3, wherein the surface of the tissue is lubricated.

20. The method of claim 19, wherein the tissue is selected from the group consisting of cartilage, synovium, meniscus, tendon, lung pleura, pericardium, and peritoneum.

* * * * *